United States Patent
Sih et al.

(10) Patent No.: US 7,885,710 B2
(45) Date of Patent: ***Feb. 8, 2011

(54) METHOD AND APPARATUS FOR TISSUE PROTECTION AGAINST ISCHEMIA USING REMOTE CONDITIONING

(75) Inventors: Haris J. Sih, Minneapolis, MN (US); Tamara Colette Baynham, Blaine, MN (US); Darrell O. Wagner, Isanti, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 493 days.

This patent is subject to a terminal disclaimer.

(21) Appl. No.: 11/318,263

(22) Filed: Dec. 23, 2005

(65) Prior Publication Data

US 2007/0150005 A1    Jun. 28, 2007

(51) Int. Cl.
*A61N 1/372* (2006.01)
(52) U.S. Cl. ........................................................ 607/3
(58) Field of Classification Search .................. 607/1–3
See application file for complete search history.

(56) References Cited

U.S. PATENT DOCUMENTS

| | | | |
|---|---|---|---|
| 5,007,427 A | 4/1991 | Suzuki et al. | |
| 5,072,458 A | 12/1991 | Suzuki | |
| 5,111,818 A | 5/1992 | Suzuki et al. | |
| 5,135,004 A | 8/1992 | Adams et al. | |
| 5,199,428 A * | 4/1993 | Obel et al. | 607/44 |
| 5,313,953 A | 5/1994 | Yomtov et al. | |
| 5,376,106 A | 12/1994 | Stahmann et al. | |
| 5,531,768 A | 7/1996 | Alferness | |
| 5,824,021 A * | 10/1998 | Rise | 607/46 |
| 6,108,577 A | 8/2000 | Benser | |
| 6,151,525 A | 11/2000 | Soykan et al. | |

(Continued)

FOREIGN PATENT DOCUMENTS

WO    WO-0128625    4/2001

(Continued)

OTHER PUBLICATIONS

Zhi-Qing Zhao, Joel S. Corvera, Michael E. Halkos, Faraz Kerendi, Ning-Ping Wang, Robert A. Guyton and Jakob Vinten-Johansen Am J Physiol Heart Circ Physiol 285:579-588, 2003. First published Apr. 3, 2003.*

(Continued)

*Primary Examiner*—Scott M Getzow
*Assistant Examiner*—Amanda Patton
(74) *Attorney, Agent, or Firm*—Schwegman, Lundberg & Woessner, P.A.

(57) ABSTRACT

A stimulation system delivers stimulation to protect an ischemic region of a body from tissue damage caused by ischemia. The stimulation is delivered to one or more stimulation sites remote from the ischemic region to elicit a physiological effect that protects the ischemic region from the tissue damage caused by ischemia. In one embodiment, the stimulation system delivers cardioprotective stimulation to one or more stimulation sites remote from the heart to protect the heart from injuries associated with cardiac ischemic events. In another embodiment, the stimulation system delivers remote conditioning stimulation to one or more stimulation sites in or on the heart to protect a non-cardiac region from injuries associated with non-cardiac ischemic events.

32 Claims, 10 Drawing Sheets

U.S. PATENT DOCUMENTS

| | | |
|---|---|---|
| 6,231,516 B1 | 5/2001 | Keilman et al. |
| 6,272,379 B1 | 8/2001 | Fischell et al. |
| 6,368,284 B1 | 4/2002 | Bardy |
| 6,408,208 B1 | 6/2002 | Sun |
| 6,423,705 B1 | 7/2002 | Tracey et al. |
| 6,445,953 B1 | 9/2002 | Bulkes et al. |
| 6,463,323 B1 | 10/2002 | Conrad et al. |
| 6,501,983 B1 | 12/2002 | Natarajan et al. |
| 6,610,713 B2 | 8/2003 | Tracey |
| 6,628,988 B2 | 9/2003 | Kramer et al. |
| 6,702,720 B2 | 3/2004 | Dardik |
| 6,783,979 B2 | 8/2004 | Rosen et al. |
| 6,827,690 B2 | 12/2004 | Bardy |
| 6,838,471 B2 | 1/2005 | Tracey |
| 6,842,642 B2 | 1/2005 | Vanhout |
| 6,845,267 B2 * | 1/2005 | Harrison et al. ............. 607/3 |
| 6,849,611 B2 | 2/2005 | Rosen et al. |
| 6,892,095 B2 | 5/2005 | Salo |
| 6,907,285 B2 | 6/2005 | Denker et al. |
| 6,913,577 B2 | 7/2005 | Bardy |
| 6,937,899 B2 | 8/2005 | Sheldon et al. |
| 7,010,345 B2 * | 3/2006 | Hill et al. ............. 607/10 |
| 7,039,462 B2 | 5/2006 | Pastore et al. |
| 7,072,711 B2 | 7/2006 | Girouard et al. |
| 7,171,258 B2 | 1/2007 | Goode |
| 7,215,992 B2 | 5/2007 | Stahmann et al. |
| 7,215,997 B2 * | 5/2007 | Yu et al. ............. 607/18 |
| 7,299,087 B2 | 11/2007 | Bardy |
| 7,340,303 B2 | 3/2008 | Zhu |
| 7,364,547 B2 | 4/2008 | Stahmann et al. |
| 7,460,906 B2 | 12/2008 | Libbus |
| 7,479,112 B2 | 1/2009 | Sweeney et al. |
| 7,486,991 B2 | 2/2009 | Libbus et al. |
| 7,774,057 B2 | 8/2010 | Pastore et al. |
| 2002/0072777 A1 | 6/2002 | Lu |
| 2002/0082660 A1 | 6/2002 | Stahmann et al. |
| 2002/0123772 A1 | 9/2002 | Sun et al. |
| 2002/0143369 A1 * | 10/2002 | Hill et al. ............. 607/9 |
| 2003/0004549 A1 | 1/2003 | Hill et al. |
| 2003/0045908 A1 | 3/2003 | Condie et al. |
| 2003/0060854 A1 | 3/2003 | Zhu |
| 2003/0120313 A1 | 6/2003 | Begemann et al. |
| 2003/0139778 A1 | 7/2003 | Fischell et al. |
| 2003/0158584 A1 * | 8/2003 | Cates et al. ............. 607/2 |
| 2003/0204206 A1 | 10/2003 | Padua et al. |
| 2003/0233130 A1 | 12/2003 | Padmanabhan et al. |
| 2004/0071637 A1 | 4/2004 | Elia |
| 2004/0088017 A1 | 5/2004 | Sharma et al. |
| 2004/0102815 A1 | 5/2004 | Balczewski et al. |
| 2004/0106961 A1 | 6/2004 | Siejko et al. |
| 2004/0132190 A1 * | 7/2004 | Dillmann et al. ............. 435/456 |
| 2004/0230240 A1 | 11/2004 | Sun et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0043675 A1 | 2/2005 | Pastore et al. |
| 2005/0096706 A1 | 5/2005 | Salo |
| 2005/0113705 A1 | 5/2005 | Fischell et al. |
| 2005/0143779 A1 | 6/2005 | Libbus |
| 2005/0149129 A1 | 7/2005 | Libbus et al. |
| 2005/0197674 A1 | 9/2005 | McCabe et al. |
| 2005/0283195 A1 | 12/2005 | Pastore et al. |
| 2005/0288721 A1 | 12/2005 | Girouard et al. |
| 2006/0015146 A1 | 1/2006 | Girouard et al. |
| 2006/0110374 A1 * | 5/2006 | Czeiger et al. ............. 424/93.7 |
| 2006/0116593 A1 | 6/2006 | Zhang et al. |
| 2006/0148737 A1 | 7/2006 | Harmon |
| 2006/0149326 A1 | 7/2006 | Prinzen et al. |
| 2006/0206158 A1 | 9/2006 | Wu et al. |
| 2006/0247686 A1 | 11/2006 | Girouard et al. |
| 2006/0247700 A1 | 11/2006 | Jackson |
| 2006/0259087 A1 | 11/2006 | Baynham et al. |
| 2006/0259088 A1 | 11/2006 | Pastore et al. |
| 2006/0282000 A1 | 12/2006 | Zhang et al. |
| 2006/0287684 A1 | 12/2006 | Baynham et al. |
| 2007/0043393 A1 | 2/2007 | Brockway et al. |
| 2007/0049835 A1 | 3/2007 | Goode |
| 2007/0054871 A1 | 3/2007 | Pastore et al. |
| 2007/0078507 A1 | 4/2007 | Zacouto |
| 2007/0150015 A1 | 6/2007 | Zhang et al. |
| 2007/0162081 A1 | 7/2007 | Yu et al. |
| 2007/0179392 A1 | 8/2007 | Zhang |
| 2007/0203524 A1 | 8/2007 | Sheldon et al. |
| 2007/0282380 A1 | 12/2007 | Brooke et al. |
| 2007/0299356 A1 | 12/2007 | Wariar et al. |
| 2008/0058661 A1 | 3/2008 | Bardy |
| 2008/0058881 A1 | 3/2008 | Wagner et al. |
| 2008/0081354 A1 | 4/2008 | Qu et al. |
| 2008/0082135 A1 | 4/2008 | Arcot et al. |
| 2008/0091138 A1 | 4/2008 | Pastore et al. |
| 2008/0132972 A1 | 6/2008 | Shuros et al. |
| 2008/0140141 A1 | 6/2008 | Ben-David et al. |
| 2008/0177156 A1 | 7/2008 | Zhang et al. |
| 2008/0177191 A1 | 7/2008 | Patangay et al. |
| 2008/0177194 A1 | 7/2008 | Zhang et al. |
| 2009/0025459 A1 | 1/2009 | Zhang et al. |
| 2009/0048641 A1 | 2/2009 | Libbus |
| 2009/0082781 A1 | 3/2009 | Tran et al. |
| 2009/0124916 A1 | 5/2009 | Sweeney et al. |
| 2009/0143835 A1 | 6/2009 | Pastore et al. |
| 2010/0121391 A1 | 5/2010 | Brockway et al. |

FOREIGN PATENT DOCUMENTS

| | | | |
|---|---|---|---|
| WO | WO-2005/046790 | | 5/2005 |
| WO | WO-2006121842 A2 | | 11/2006 |

OTHER PUBLICATIONS

"U.S. Appl. No. 11/129,050, Non-Final Office Action mailed Nov. 26, 2007", 7 pgs.

"U.S. Appl. No. 11/129,050, Response filed Feb. 26, 2008, to Non-Final Office Action mailed Nov. 26, 2007", 14 pgs.

"U.S. Appl. No. 11/129,050, Final Office Action mailed May 12, 2008", 9 pgs.

Rosa, A., et al., "Ectopic Pacing at Physiological Rate Improves Postanoxic Recovery of the Developing Heart", *Am. J. Physiol.—Heart Circ. Physiol., 284*, (2003),H2384-H2392.

"U.S. Appl. No. 11/129,050, Response filed Sep. 28, 2007 to Restriction Requirement mailed Aug. 1, 2007", 11 pgs.

"U.S. Appl. Serial No. 11/129,058 Final Office Action Received Jul. 9, 2007", 17 pgs.

"U.S. Appl. No. 11/129,058 Non Final office action mailed Jan. 29, 2007", 12 pgs.

"U.S. Appl. No. 11/129,058 Response filed Apr. 30, 2007 to Non Final office action mailed Jan. 29, 2007", 16 pgs.

"U.S. Appl. No. 11/129,058, Response filed Oct. 9, 2007 to Final Office Action mailed Jul. 9, 2007", 14 pgs.

"Non-Final Office Action mailed by the USPTO on Mar. 31, 2006 for related matter U.S. Appl. No. 10/788,906", 41 Pages.

"Non-Final Office Action Response Filed Jun. 30, 2006 with the USPTO for related matter U.S. Appl. No. 10/788,906", 26 Pages.

"Restriction Requirement Mailed Aug. 1, 2007 U.S. Appl. No. 11/129,050", RERR,6 pgs.

Birnbaum, Y, et al., "Ischemic preconditioning at a distance: reduction of myocardial infarct size by partial reduction of blood supply combined with rapid stimulation of the gastrocnemius muscle in the rabbit.", *Circulation, 96(5)*, (Sep. 7, 1997), 1641-6.

Carlson, Gerrard M., et al., "Hemodynamic Stability Assessment Based on Heart Sounds", U.S. Appl. No. 11/277,773, filed Mar. 29, 2006, 39 Pages.

Dzwonczyk, R., et al., "Myocardial electrical impedance responds to ischemia and reperfusion in humans", *IEEE Transactions on Biomedical Engineering, 51(12)*, (Dec. 2004),2206-2209.

Er, F., et al., "Dominant-negative suppression of HCN channels markedly reduces the native pacemaker current I(f) and undermines spontaneous beating of neonatal cardiomyocytes.", *Circulation*, 107(3), (Jan. 2003),485-9.

Ishihara, M., et al., "Implications of prodromal angina pectoris in anterior wall acute myocardial infarction: acute angiographic findings and long-term prognosis", *J Am Coll Cardiol.*, 30(4), (1997),970-5.

Kloner, R. A., et al., "Prospective temporal analysis of the onset of preinfarction angina versus outcome: an ancillary study in TIMI-9B", *Circulation*, 97(11), (1998),1042-5.

Krayenbuhl, H. P., "Hemodynamics in ischemia. Systolic phase", *Z. Kardiol.*, 73 Suppl 2, [Article in German with English Abstract], (1984), 119-25.

Loukogeorgakis, S. P., et al., "Remote ischemic preconditioning provides early and late protection against endothelial ischemia-reperfusion injury in humans: role of the autonomic nervous system.", *J Am Coll Cardiol.*, 46(3), (Aug. 2, 2005),450-6.

Melo, L. G., et al., "Molecular and cell-based therapies for protection, rescue, and repair of ischemic myocardium: reasons for cautious optimism.", *Circulation*, 109(20), (May 2004),2386-93.

Murry, C. E., "Preconditioning with ischemia: a delay of lethal cell injury in ischemic myocardium", *Circulation*, 74(5), (1986),1124-1136.

Ovize, M., et al., "Stretch preconditions canine myocardium.", *Am J Physiol.*, 266(1 Pt 2), (Jan. 1994),H137-46.

Patangay, Ahilash, et al., "Ischemia Detection Using Heart Sound Timing", U.S. Appl. No. 11/625,003, filed Jan. 19, 2007, 69 Pages.

Prinzen, Frits W., "Mapping of regional myocardial strain and work during ventricular pacing: experimental study using magnetic resonance imaging tagging", *Journal of the American College of Cardiology*, 33(6), (May 1999),1735-1742.

Qu, J, et al., "HCN2 overexpression in newborn and adult ventricular myocytes: distinct effects on gating and excitability", *Circ. Res.*, vol. 89(1), (Jul. 6, 2001),e8-14.

Schoemaker, R. G., et al., "Bradykinin mediates cardiac preconditioning at a distance", *Am J Physiol Heart Circ Physiol.*, 278(5), (May 2000),H1571-6.

Solomon, S. D., et al., "Angina pectoris prior to myocardial infarction protects against subsequent left ventricular remodeling", *J Am Coll Cardiol.*, 43(9), (2004),1511-4.

Wariar, Ramesh, et al., "Detection of Myocardial Ischemia From the Time Sequence of Implanted Sensor Measurements", U.S. Appl. No. 11/426,835, filed Jun. 27, 2006, 41 Pages.

Zhao, Zhi-Qing, et al., "Inhibition of myocardial injury by ischemic postconditioning during reperfusion: comparison with ischemic preconditioning", *Am J Physiol Heart Circ Physiol*, 285(2), (Aug. 2003),H579-H588.

"U.S. Appl. No. 11/129,050, Advisory Action mailed Jul. 28, 2008", 3 pgs.

"U.S. Appl. No. 11/129,050, Response filed Jul. 14, 2008 to Final Office Action mailed May 12, 2008", 13 pgs.

"U.S. Appl. No. 11/129,050, Supplemental Amendment and Response filed Sep. 12, 2008 to Final Office Action mailed May 12, 2008 and the Advisory Action mailed Jul. 28, 2008", 12 pgs.

"U.S. Appl. No. 11/129,050 Non-Final Office Action mailed Nov. 6, 2008", 8 pgs.

"U.S. Appl. No. 11/129,058, Advisory Action mailed Oct. 17, 2007", 3 pgs.

"U.S. Appl. No. 11/129,058, Appeal Brief filed Jan. 8, 2008", 22 pgs.

"U.S. Appl. No. 11/129,058, Examiner's Answer mailed Jun. 18, 2008", 14 pgs.

"U.S. Appl. No. 11/129,050, Response filed Feb. 23, 2009 to Non Final Office Action mailed Nov. 6, 2008", 13 pgs.

"U.S. Appl. No. 11/129,050, Final Office Action mailed Apr. 21, 2009", 11 pgs.

"U.S. Appl. No. 11/220,397, Non-Final Office Action mailed Dec. 22, 2008", 14 pgs.

"U.S. Appl. No. 11/220,397, Response filed Mar. 23, 2008 to Non Final Office Action mailed Dec. 22, 2008", 14 pgs.

"U.S. Appl. No. 11/113,828, Non-Final Office Action mailed Mar. 5, 2008, 8 pgs", 9 pgs.

"U.S. Appl. No. 11/129,050, Advisory Action mailed Jul. 14, 2009", 3 pgs.

"U.S. Appl. No. 11/129,050, Response filed Jun. 22, 2009 to Final Office Action mailed Apr. 21, 2009", 9 pgs.

"U.S. Appl. No. 11/220,397, Final Office Action mailed May 22, 2009", 12 pgs.

"U.S. Appl. No. 11/318,263, Restriction Requirement mailed Jul. 14, 2009", 5 pgs.

"U.S. Appl. No. 11/129,050, Notice of Allowance mailed Aug. 24, 2009", 7 pgs.

"U.S. Appl. No. 11/129,058, Decision on Appeal mailed Nov. 4, 2009", 15 pgs.

"U.S. Appl. No. 11/220,397, Response filed Aug. 24, 2009, to Final Office Action mailed May 22, 2009", 12 pgs.

"U.S. Appl. No. 11/129,050 Notice of Allowance mailed Jul. 16, 2010", 4 pgs.

"U.S. Appl. No. 11/129,050, Interview Summary mailed Feb. 11, 2009", 2 pgs.

"U.S. Appl. No. 11/129,050, Notice of Allowance mailed Apr. 1, 2010", 6 pgs.

"U.S. Appl. No. 11/129,058, Office Communication mailed Jan. 15, 2010", 2 pgs.

"U.S. Appl. No. 11/220,397, Notice of Allowance mailed Mar. 30, 2010", 6 pgs.

Pastore, J. M., et al., "Method and Apparatus for Device Controlled Gene Expression for Cardiac Protection", U.S. Appl. No. 12/830,534, filed Jul. 6, 2010, 64 pgs.

\* cited by examiner

METHOD AND APPARATUS FOR TISSUE PROTECTION AGAINST ISCHEMIA USING REMOTE CONDITIONING

CROSS-REFERENCE TO RELATED APPLICATIONS

This application is related to commonly assigned, U.S. patent application Ser. No. 11/220,397, entitled "METHOD AND APPARATUS FOR DEVICE CONTROLLED GENE EXPRESSION FOR CARDIAC PROTECTION," filed on Sep. 6, 2005, now U.S. Pat. No. 7,774,057, U.S. patent application Ser. No. 11/207,251, entitled "METHOD AND APPARATUS FOR DELIVERING CHRONIC AND POST-ISCHEMIA CARDIAC THERAPIES," filed on Aug. 19, 2005, now U.S. Pat. No. 7,668,594, U.S. patent application Ser. No. 11/129,058, entitled "METHOD AND APPARATUS FOR DELIVERING PACING PULSES USING A CORONARY STENT," filed on May 13, 2005, now abandoned, and U.S. patent application Ser. No. 11/129,050, entitled "METHOD AND APPARATUS FOR CARDIAC PROTECTION PACING," filed on May 13, 2005, which are hereby incorporated herein by reference in their entirety.

TECHNICAL FIELD

This document relates generally to medical devices and particularly to a system for protecting the heart from injuries associated with cardiac ischemic events by delivering stimulation to one or more sites remote from the ischemic region.

BACKGROUND

Ischemia is a condition in which portions of a body are deprived of adequate oxygen and metabolite removal due to an interruption in blood supply caused by an occlusion of a blood vessel. The inadequate oxygen supply and metabolite removal cause tissue injury that may result in impaired physiological functions of an organ to which the adequate blood flow is interrupted. One example of ischemia is cardiac ischemia, a condition in which the myocardium is deprived of adequate supply of blood due to occlusion of a blood vessel such as a coronary artery.

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium. In a normal heart, the sinoatrial node, the heart's natural pacemaker, generates electrical impulses that propagate through an electrical conduction system to various regions of the heart to excite the myocardial tissues of these regions. Coordinated delays in the propagations of the electrical impulses in a normal electrical conduction system cause the various portions of the heart to contract in synchrony to result in efficient pumping functions. A blocked or otherwise abnormal electrical conduction and/ or deteriorated myocardial tissue cause dysynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure, as well as a risk of suffering recurrent MI.

Therefore, there is a need to protect tissue from ischemic damage, including the need to protect the heart from injuries associated with cardiac ischemic events.

SUMMARY

A stimulation system delivers stimulation to protect an ischemic region of a body from tissue damage caused by ischemia. The stimulation is delivered to one or more stimulation sites remote from the ischemic region to elicit a physiological effect that protects the ischemic region from the tissue damage caused by ischemia.

In one embodiment, a cardioprotective stimulation system includes at least one stimulation output device coupled to an implantable medical device. The stimulation output device is configured for placement in a stimulation site remote from the heart. The implantable medical device includes a cardioprotective stimulation module and a cardioprotective stimulation controller. The cardioprotective stimulation module delivers one or more non-cardiac stimuli to the stimulation site through the stimulation output device. The one or more non-cardiac stimuli are capable of eliciting a cardioprotective effect against cardiac ischemia without causing myocardial contraction. The cardioprotective stimulation controller includes a stimulation initiator and a stimulation timer. The stimulation initiator produces cardioprotective stimulation signals. In response to each of the cardioprotective stimulation signals, the stimulation timer times a cardioprotective stimulation sequence. The cardioprotective stimulation sequence includes alternating stimulation and non-stimulation periods. The stimulation periods each have a stimulation duration during which the one or more non-cardiac stimuli are delivered. The non-stimulation periods each have a non-stimulation duration during which no non-cardiac stimulus is delivered.

In one embodiment, a method for operating an implantable medical device for cardioprotection against cardiac ischemia is provided. A cardioprotective stimulation signal is received. In response to the cardioprotective stimulation signal, a cardioprotective stimulation sequence is timed. The cardioprotective stimulation sequence includes alternating stimulation and non-stimulation periods. The stimulation periods each have a stimulation duration during which one or more non-cardiac stimuli are delivered. The non-stimulation periods each have a non-stimulation duration during which no non-cardiac stimulus is delivered. The one or more non-cardiac stimuli are delivered from the implantable medical device to at least one stimulation site remote from the heart during each of the stimulation period. The one or more non-cardiac stimuli are capable of eliciting a cardioprotective effect against cardiac ischemia without causing myocardial contraction.

In one embodiment, an implantable medical device includes a cardiac electrical stimulation circuit and a cardiac stimulation controller. The cardiac electrical stimulation circuit delivers pacing pulses to a cardiac location. The cardiac stimulation controller initiates and times a remote conditioning stimulation sequence in response to a therapy initiation event. The remote conditioning stimulation sequence includes alternating pacing and non-pacing periods. The pacing pulses are delivered during each of the pacing periods at a pacing rate that is sufficiently high to elicit a physiological effect that protects a non-cardiac ischemic region from ischemic tissue damage by inducing cardiac ischemia. No pacing pulse is delivered during the non-pacing periods.

In one embodiment, a method for operating an implantable medical device to perform remote conditioning to protect a non-cardiac ischemic region from ischemic damage by stimulating the heart is provided. A remote conditioning stimulation sequence is initiated in response to a therapy initiation event. The remote conditioning stimulation sequence includes alternating pacing and non-pacing periods. Cardiac pacing pulses are delivered during each of the pacing periods at a pacing rate that is sufficiently high to elicit a physiological effect that protects the non-cardiac ischemic region from ischemic tissue damage by inducing cardiac ischemia.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
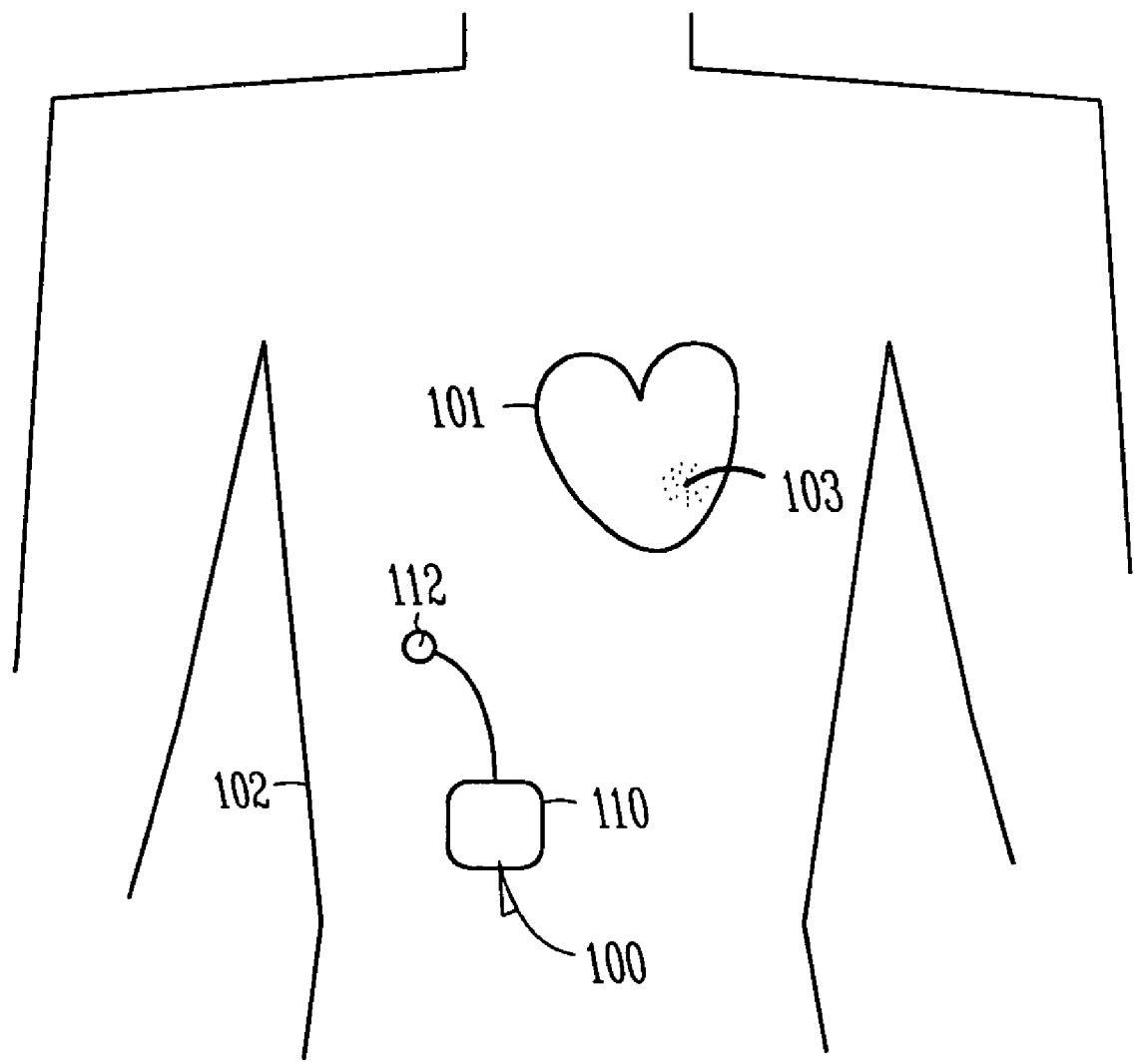
FIG. 1 is an illustration of an embodiment of a stimulation system and portions of an environment in which the stimulation system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a stimulation system providing for remote conditioning that elicits physiological protective effect against ischemic damage. The stimulation system protects an ischemic region of a body from tissue damage caused by ischemia by delivering stimulation to one or more stimulation sites in or on the body but remote from the ischemic region.

One example of a stimulation system according to the present subject matter includes an implantable medical device that delivers cardioprotective stimulation (also known as cardiac protection stimulation) to protect the heart from injuries associated with cardiac ischemic events, including MI. Cardioprotective therapies delivered to a heart, such as ischemic postconditioning, ischemic preconditioning, pacing postconditioning, and pacing preconditioning, have shown cardioprotective effects by reducing myocardial tissue damage caused by ischemic events, including MI. Ischemic postconditioning protects the myocardium by inducing brief periods of ischemia after an ischemic event is detected. Ischemic preconditioning is a prophylactic therapy that protects the myocardium from an anticipated or predicted ischemic event by inducing brief periods of ischemia before the occurrence of the ischemic event. Pacing postconditioning protects the myocardium by delivering brief periods of a pacing therapy to the heart after an ischemic event is detected. Pacing preconditioning is a prophylactic therapy that protects the myocardium from an anticipated or predicted ischemic event by brief periods of a pacing therapy to the heart before the occurrence of such ischemic event. One specific example of pacing preconditioning is to deliver brief periods of pacing therapy to protect the myocardium from potentially recurring ischemic events after the pacing postconditioning has been delivered. In additions to such cardioprotective therapies delivered to a heart, ischemic preconditioning therapy delivered to a region in the body at a distance from the heart have also shown cardioprotective effects against cardiac ischemia.

According to the present subject matter, the cardioprotective stimulation includes delivery of one or more stimuli to one or more stimulation sites in the body of a patient to elicit a cardioprotective effect against cardiac ischemia. The one or more stimulation sites are remote from the patient's heart and/or in the patient's heart but remote from any cardiac ischemic region. The one or more stimuli may create a physiologic stress in the one or more stimulation sites, and the physiologic stress triggers an intrinsic myocardial protective mechanism against ischemic damage to the myocardial tissue. In one embodiment, the implantable medical device detects cardiac ischemic events. In response to the detection of a cardiac ischemic event, a cardioprotective stimulation sequence is initiated to protect the heart from ischemic damage caused by the detected cardiac ischemic event. Then, additional cardioprotective stimulation sequences are initiated to protect the heart from ischemic damage caused by potentially recurrent cardiac ischemic events. In another embodiment, the implantable medical device receives a cardioprotective stimulation command. In response, a cardioprotective stimulation sequence is initiated. The cardioprotective stimulation command is issued by a physician or other caregiver or the patient in response to a cardiac ischemic event that has occurred or a diagnosis classifying the patient as having a high risk of cardiac ischemia or MI. Examples of indications of high risk of cardiac ischemia or MI include coronary artery disease (CAD), previous MI, unstable angina, and vulnerable plaque. In one embodiment, each cardioprotective stimulation sequence includes alternating stimulation and non-stimulation periods. The stimulation periods each have a stimulation duration during which one or more stimuli are delivered. The non-stimulation periods each have a non-stimulation duration during which no stimulus is delivered. In other words, the cardioprotective stimulation sequence includes intermittent stimulation over a predetermined duration. The stimulation is delivered in any form of energy that is capable eliciting a cardioprotective effect against ischemic damage to the myocardial tissue. Examples of such stimulation include electrical stimulation, mechanical stimulation, chemical stimulation, biologic stimulation, optical stimulation, thermal stimulation, and acoustic stimulation.

While implantable medical devices are specifically discussed in this document as examples of a device that delivers cardioprotective stimulation, the present subject matter is not limited to implantable medical devices. In general, the cardioprotective stimulation according to the present subject matter can be delivered by any implantable or non-implantable medical devices that are capable of delivering any form of stimulation that elicits cardioprotective effect against cardiac ischemia from any location in a body remote from the cardiac ischemic region(s).

While cardioprotective stimulation is specifically discussed in this document as an example of remote conditioning for tissue protection against ischemia, the present subject matter is not limited to cardioprotective stimulation. Other examples of a stimulation system according to the present subject matter include stimulation devices that deliver stimulation to protect non-cardiac tissue or organ against ischemic damage. Specific examples of such stimulation devices include a stimulator for protection against tissue damage caused by ischemic stroke, a stimulator for protection against damage to a kidney caused by ischemic renal failure, a stimulator for protection against neural damage caused by ischemia in the central nervous system, and a stimulator for protection against muscular damage caused by ischemia in skeletal muscle. In one embodiment, the remote conditioning for tissue protection against ischemia is performed by electrically stimulating the heart to elicit protective effects in tissue remote from the heart. This allows a cardiac stimulation device such as an implantable pacemaker to deliver a therapy that protects a non-cardiac organ from ischemic damage. For example, pacing pulses may be delivered to the heart at a rate that is sufficiently high to induce transient cardiac ischemia. Through the autonomic nervous system, the transient cardiac ischemia elicits protective effects against ischemic injury in other organs innervated by the autonomic nervous system. In general, the stimulation according to the present subject matter can be delivered by any implantable or non-implantable medical devices that are capable of delivering any form of stimulation that elicits physiological protective effect against ischemic damage from any location in a body remote from the region(s) wherein ischemia occurs in the body.

FIG. 1 is an illustration of an embodiment of a stimulation system 100 and portions of an environment in which system 100 is used. In the embodiment illustrated in FIG. 1, system 100 is a cardioprotective stimulation system. In various other embodiments, system 100 includes a stimulation system that delivers stimulation to one or more stimulation sites remote from an injured region to protect the injured region from ischemic damage. As illustrated in FIG. 1, system 100 includes an implantable medical device 110 and a stimulation output device 112. As illustrated in FIG. 1, system 100 is implanted in a patient's body 102 having a heart 101. Heart 101 has an ischemic region 103 that includes ischemic tissue resulted from a cardiac ischemic event, such as an acute MI.

Stimulation output device 112 is placed in a location in body 102 that is remote from ischemic region 103. Implantable medical device 110 includes an implantable housing that contains a stimulation module that delivers one or more stimuli through stimulation output device 112. The one or more stimuli elicit a cardioprotective effect that reduces ischemic damage in and around ischemic region 103. Stimulation output device 112 is connected to implantable medical device 110 directly or through a lead that allow transmission of the one or more stimuli.

In one embodiment, as illustrated in FIG. 1, stimulation device output device 112 is placed in a location in body 102 that is remote from heart 101. The one or more stimuli that elicit the cardioprotective effect are one or more non-cardiac stimuli. Implantable medical device 110 includes a non-cardiac stimulation module that delivers the one or more non-cardiac stimuli through stimulation output device 112. The one or more non-cardiac stimuli elicit a cardioprotective effect that reduces ischemic damage in and around ischemic region 103 without causing myocardial contraction in heart 101. That is, the one or more non-cardiac stimuli are delivered to a stimulation site remote from the heart and do not activate the heart as pacing, cardioversion, or defibrillation does.

In one embodiment, implantable medical device 110 is a dedicated cardioprotective stimulator that delivers the one or more stimuli eliciting the cardioprotective effect. In various other embodiments, implantable medical device 110 is an implantable device including the functionality of cardioprotective stimulation. Examples of such an implantable device include a CRM device (such as a pacemaker, a cardioverter/defibrillator, and a cardiac resynchronization therapy device), a neural stimulator that provides for sympathetic and/or parasympathetic neural stimulation, a muscular stimulator, a neuromuscular stimulator, a drug delivery device, a biologic therapy device, and a physiological monitor.

In various embodiments in which system 100 is used to protect non-cardiac tissue or organs against ischemic damage, implantable medical device 110 includes one or more of a stimulator that protects neural or other tissue from ischemic stroke, a stimulator that protects kidney(s) from ischemic renal failure, a stimulator that protects neural tissue from ischemia in the central nervous system, and a stimulator that protects muscular tissue from ischemia in skeletal muscle. In one embodiment, implantable medical device 110 includes a cardiac stimulation device that delivers one or more therapies to protect non-cardiac tissue or organs against ischemic damage by delivering electrical stimulation pulses to the heart. In a specific embodiment, the cardiac stimulation device is a CRM device that is capable of delivering cardiac therapies, cardioprotective therapies, and/or remote conditioning therapies. For example, the cardiac stimulation device delivers cardiac therapies such as pacing therapies on a long-term basis. In response to the detection of a cardiac ischemic event, the cardiac stimulation device delivers a cardioprotective therapy. In response to the detection of an ischemic event in a non-cardiac location of the body, the cardiac stimulation device delivers a remote conditioning therapy by eliciting protective effects through the autonomic nervous system.

Figure 2:
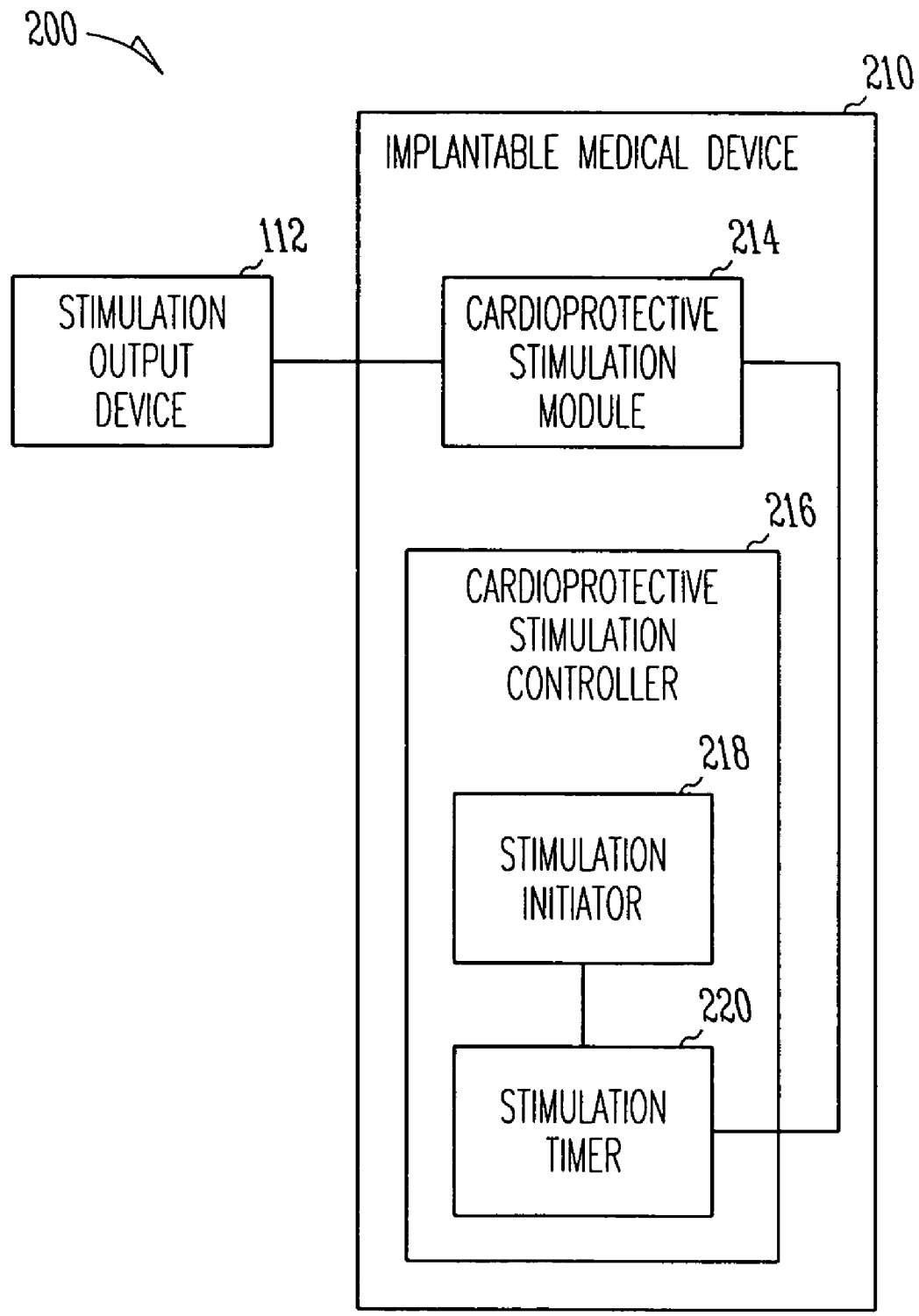
FIG. 2 is a block diagram illustrating an embodiment of portions of a circuit of a cardioprotective stimulation system.

FIG. 2 is a block diagram illustrating an embodiment of portions of a circuit of a cardioprotective stimulation system 200. System 200 is a specific embodiment of system 100 and includes stimulation output device 112 and an implantable medical device 210.

Stimulation output device 112 provides for an interface between implantable medical device 210 and tissue at one or more stimulation sites in body 102. The interface allows delivery of cardioprotective stimulation into the tissue. Stimulation output device 112 is configured for placement in the one or more stimulation sites, which are locations in body 102 that are remote from ischemic region 103. Stimulation output device 112 is connected to implantable medical device 210. In one embodiment, stimulation output device 112 is connected to implantable medical device 210 through a lead. In another embodiment, stimulation output device 112 is physically attached to implantable medical device 210, such as incorporated onto the housing of implantable medical device 210. In another embodiment, stimulation output device 112 is part of implantable medical device 210, such as a portion of implantable medical device 210 that provides for an interface through which cardioprotective stimulation is delivered into tissue.

Implantable medical device 210 is a specific embodiment of implantable medical device 110 and includes a cardioprotective stimulation module 214 and a cardioprotective stimulation controller 216. Cardioprotective stimulation module 214 delivers one or more stimuli into tissue at the one or more stimulation sites through stimulation output device 112. The one or more stimuli are capable of eliciting a cardioprotective effect against cardiac ischemia. Examples of such one or more stimuli includes one or more stimuli creating a physiologic stress at the one or more stimulation sites, one or more stimuli creating a local ischemic condition at the one or more stimulation sites, and one or more stimuli causing a release of one or more cardioprotective paracrine factors. Cardioprotective stimulation controller 216 controls the delivery of the one or more stimuli and includes a stimulation initiator 218 and a stimulation timer 220. Stimulation initiator 218 produces cardioprotective stimulation signals each initiating a cardioprotective stimulation sequence. In various embodiments, stimulation initiator 218 produces cardioprotective stimulation signals in response to a predetermined event sensed by implantable medical device 210 or a predetermined command received by implantable medical device 210. Stimulation timer 220 times the cardioprotective stimulation sequence. The cardioprotective stimulation sequence includes alternating stimulation and non-stimulation periods. Each stimulation period has a stimulation duration during which the one or more stimuli are delivered to the one or more stimulation sites. Each non-stimulation period has a non-stimulation duration during which none of the one or more stimuli is delivered to the one or more stimulation sites.

Figure 3:
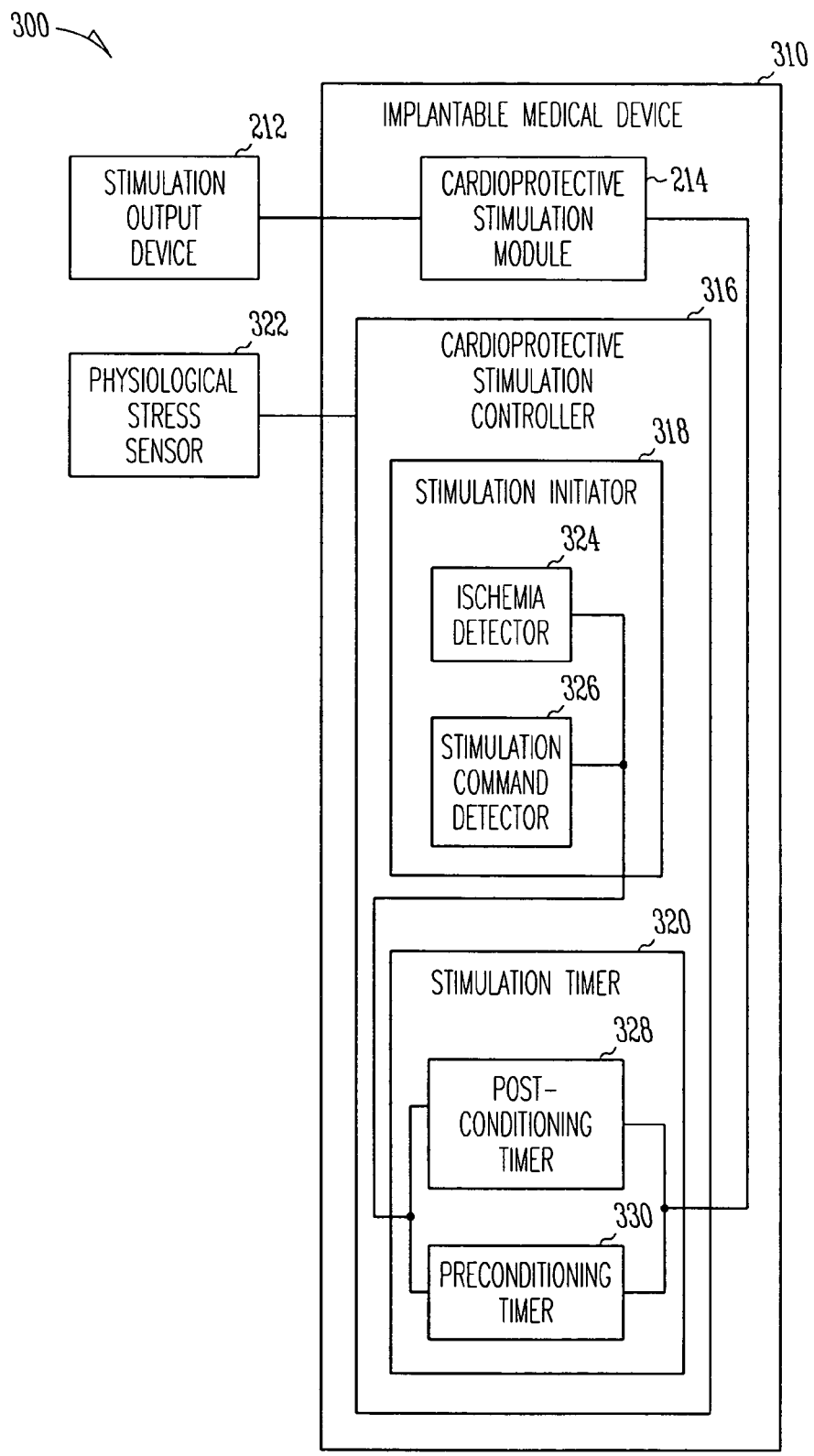
FIG. 3 is a block diagram illustrating a specific embodiment of portions of the circuit of the cardioprotective stimulation system.

FIG. 3 is a block diagram illustrating a specific embodiment of portions of the circuit of a cardioprotective stimulation system 300, which is a specific embodiment of cardioprotective stimulation system 200. Cardioprotective stimulation system 300 includes stimulation output device 212, an implantable medical device 310, and a physiological stress sensor 322.

Implantable medical device 310 is a specific embodiment of implantable medical device 210 and includes cardioprotective stimulation module 214 and a cardioprotective stimulation controller 316. Cardioprotective stimulation controller 316 is a specific embodiment of cardioprotective stimulation controller 216 and includes a stimulation initiator 318 and a stimulation timer 320. Stimulation initiator 318 is a specific embodiment of stimulation initiator 218 and produces the cardioprotective stimulation signals in response to a detected cardiac ischemic event and/or a command sent by a physician or other caregiver or the patient.

In the embodiment illustrated in FIG. 3, stimulation initiator 318 includes an ischemia detector 324 and a stimulation command detector 326. In various embodiments, stimulation initiator 318 includes any one or both of ischemia detector 324 and stimulation command detector 326.

Ischemia detector 324 includes an ischemia analyzer running an automatic ischemia detection algorithm to detect cardiac ischemic events from one or more signals sensed from body 102. In one embodiment, ischemia detector 324 produces an ischemia alert signal indicative of the detection of each cardiac ischemic event. The ischemia alert signal is communicated to a physician or other caregiver or the patient as an alarm signal and/or a warning message. In one embodiment, implantable medical device 310 includes a speaker to produce an audible alarm signal and/or warning message. In another embodiment, implantable medical device 310 transmits the ischemia alert signal to an external system. The external system produces the alarm signal and/or warning message to communicate to the physician or other caregiver or the patient.

In one embodiment, ischemia detector 324 detects the cardiac ischemic events from one or more cardiac signals. Ischemia detector 324 includes or communicates to a cardiac sensing circuit that senses the one or more cardiac signals. In a specific example, cardiac signals are sensed using a wearable vest including embedded electrodes configured to sense surface biopotential signals indicative of cardiac activities. The sensed surface biopotential signals are transmitted to implantable medical device 310 via telemetry. In another specific embodiment, ischemia detector 324 detects the cardiac ischemic events from one or more wireless electrocardiogram (ECG) signals. A wireless ECG is a signal approximating the surface ECG and is acquired without using surface (skin contact) electrodes. An example of a circuit for sensing the wireless ECG is discussed in U.S. patent application Ser. No. 10/795,126, entitled "WIRELESS ECG IN IMPLANTABLE DEVICES," filed on Mar. 5, 2004, assigned to Cardiac Pacemakers, Inc., which is incorporated herein by reference in its entirety. An example of a wireless ECG-based ischemia detector is discussed in U.S. patent application Ser. No. 11/079,744, entitled "CARDIAC ACTIVATION SEQUENCE MONITORING FOR ISCHEMIA DETECTION," filed on Mar. 14, 2005, assigned to Cardiac Pacemakers, Inc., which is incorporated herein by reference in its entirety. In another embodiment, ischemia detector 324 detects the cardiac ischemic events from one or more electrogram signals. Examples of an electrogram-based ischemia detector are discussed in U.S. Pat. No. 6,108, 577, entitled, "METHOD AND APPARATUS FOR DETECTING CHANGES IN ELECTROCARDIOGRAM SIGNALS," and U.S. patent application Ser. No. 09/962,852, entitled "EVOKED RESPONSE SENSING FOR ISCHEMIA DETECTION," filed on Sep. 25, 2001, both assigned to Cardiac Pacemakers, Inc., which are incorporated herein by reference in their entirety.

In another embodiment, ischemia detector 324 detects the cardiac ischemic events from one or more impedance signals. Ischemia detector 324 includes or communicates to an impedance sensing circuit that senses the one or more impedance signals each indicative of a cardiac impedance or a transthoracic impedance. Ischemia detector 324 includes an electrical impedance based sensor using a low carrier frequency to detect the cardiac ischemic events from an electrical impedance signal. Tissue electrical impedance has been shown to increase significantly during ischemia and decrease significantly after ischemia, as discussed in Dzwonczyk, et al. *IEEE Trans. Biomed. Eng.*, 99(12): 2206-09 (2004). Ischemia detector 324 senses low frequency electrical impedance signal between electrodes interposed in the heart, and detects the ischemia as abrupt changes in impedance (such as abrupt increases in value).

In another embodiment, ischemia detector 324 detects the cardiac ischemic events from one or more signals indicative of heart sounds. Ischemia detector 324 includes or communicates to a heart sound sensing circuit. The heart sound sensing circuit senses the one or more signals indicative of heart sounds using one or more sensors such as implantable accelerometers and/or microphones. Ischemia detector 324 detects the cardiac ischemic event by detecting predetermined type heart sounds, predetermined type heart sound components, predetermined type morphological characteristics of heart sounds, or other characteristics of heart sounds indicative of ischemia.

In another embodiment, ischemia detector 324 detects the cardiac ischemic events from one or more pressure signals. Ischemia detector 324 includes or communicates to a pressure sensing circuit coupled to one or more pressure sensors. In a specific embodiment, the pressure sensor is an implantable pressure sensor sensing a signal indicative of an intracardiac or intravascular pressure whose characteristics are indicative of ischemia.

In another embodiment, ischemia detector 324 detects the cardiac ischemic event from one or more acceleration signals each indicative of regional cardiac wall motion. Ischemia detector 324 includes or communicates to cardiac motion sensing circuit coupled to one or more accelerometers each incorporated into a portion of a lead positioned on or in the heart. The ischemia detector detects ischemia as an abrupt decrease in the amplitude of local cardiac accelerations.

In another embodiment, ischemia detector 324 detects the cardiac ischemic event from a heart rate variability (HRV) signal indicative of HRV. Ischemia detector 324 includes or communicates to an HRV sensing circuit that senses the HRV and produces the HRV signal, which is representative of an HRV parameter. HRV is the beat-to-beat variance in cardiac cycle length over a period of time. The HRV parameter includes any parameter being a measure of the HRV, including any qualitative expression of the beat-to-beat variance in cardiac cycle length over a period of time. In a specific embodiment, the HRV parameter includes the ratio of Low-Frequency (LF) HRV to High-Frequency (HF) HRV (LF/HF ratio). The LF HRV includes components of the HRV having frequencies between about 0.04 Hz and 0.15 Hz. The HF HRV includes components of the HRV having frequencies between about 0.15 Hz and 0.40 Hz. Ischemia detector 324 detects ischemia when the LF/HF ratio exceeds a predetermined threshold. An example of an LF/HF ratio-based ischemia detector is discussed in U.S. patent application Ser. No. 10/669,168, entitled "METHOD FOR ISCHEMIA DETECTION BY IMPLANTABLE CARDIAC DEVICE," filed on Sep. 23, 2003, assigned to Cardiac Pacemakers, Inc., which is incorporated herein by reference in its entirety.

In one embodiment, in response to a detection of the cardiac ischemic event, stimulation initiator 318 produces a postconditioning signal. The postconditioning signal is a cardioprotective stimulation signal that starts a postconditioning stimulation sequence. The postconditioning stimulation sequence is a cardioprotective stimulation sequence that follows the occurrence of a cardiac ischemic event to reduce the tissue damage associated with that cardiac ischemic event. In one embodiment, stimulation initiator 318 produces the postconditioning signal when the end of the cardiac ischemic event is detected. In a specific embodiment, the end of the cardiac ischemic event is detected when the cardiac ischemic event is no longer detected by ischemia detector 324. In another embodiment, stimulation initiator 318 produces the postconditioning signal when a post-ischemia time interval expires. The post-ischemia time interval starts when the end of the cardiac ischemic event is detected and is up to approximately 10 minutes, with approximately 30 seconds being a specific example. In one embodiment, the post-ischemia time interval is chosen such that the postconditioning stimulation sequence is initiated after the reperfusion phase following the cardiac ischemic event has started.

In a further embodiment, in addition to producing the postconditioning signal, stimulation initiator 318 produces a plurality of preconditioning signals in response to the detection of the cardiac ischemic event. Each preconditioning signal is a cardioprotective stimulation signal that starts a prophylactic preconditioning stimulation sequence. The preconditioning stimulation sequence is a cardioprotective stimulation sequence that follows the occurrence of the cardiac ischemic event to reduce potential tissue damage associated with an anticipated recurring cardiac ischemic event. Stimulation initiator 318 produces the plurality of preconditioning signals after the end of the cardiac ischemic event is detected and the postconditioning stimulation sequence is completed. In one embodiment, stimulation initiator 318 produces the plurality of preconditioning signals according to a programmed preconditioning schedule. In a specific embodiment, stimulation initiator 318 produces the plurality of preconditioning signals on a periodic basis using a predetermined period. The predetermined period is in a range of approximately 24 hours to 72 hours, with approximately 48 hours being a specific example.

Stimulation command detector 326 detects a cardioprotective stimulation command. In one embodiment, the cardioprotective stimulation command is in a form of a predetermined simple signal such as the presence of a magnetic field. The cardioprotective stimulation command triggers one or more cardioprotective stimulation sequences that have been programmed into stimulation timer 320. In another embodiment, the cardioprotective stimulation command includes a code. In a specific embodiment, the code specifies programmable parameters controlling timing and or intensity of one or more cardioprotective stimulation sequences.

In one embodiment, in response to a detection of the cardioprotective stimulation command, stimulation initiator 318 produces a cardioprotective stimulation signal. In a specific embodiment, stimulation initiator 318 produces a postconditioning signal and a plurality of preconditioning signals in response to the detection of the cardioprotective stimulation command. The postconditioning signal is produced when the cardioprotective stimulation command is detected. The plurality of preconditioning signals are produced according to a predetermined schedule, such as on a periodic basis using a predetermined period in a range of approximately 24 hours to 72 hours, with approximately 48 hours being a specific example. In another specific embodiment, stimulation initiator 318 produces a postconditioning signal when the detected cardioprotective stimulation command is a postconditioning command and produces a preconditioning signal when the detected cardioprotective stimulation command is a preconditioning command.

In one embodiment, stimulation initiator 318 produces a postconditioning signal in response to the detection of any one of the cardiac ischemic event or the cardioprotective stimulation command. If a cardiac ischemic event and a cardioprotective stimulation command are detected within a predetermined period of time, they are deemed to be associated with the same cardiac ischemic event by stimulation initiator 318.

Stimulation timer 320 is a specific embodiment of stimulation timer 220 and includes a postconditioning timer 328 and a preconditioning timer 330. Postconditioning timer 328 receives the postconditioning signal from stimulation initiator 318 and times a postconditioning stimulation sequence when the postconditioning signal is received. The postconditioning stimulation sequence includes alternating postconditioning stimulation and non-stimulation periods. The postconditioning stimulation periods each have a postconditioning stimulation duration during which one or more stimuli are delivered. The postconditioning non-stimulation periods each have a postconditioning non-stimulation duration during which no stimulus is delivered. Preconditioning timer 330 receives each of the preconditioning signals and times a preconditioning stimulation sequence when one of the postconditioning signals is received from stimulation initiator 318. The preconditioning stimulation sequence includes alternating preconditioning stimulation and non-stimulation periods. The preconditioning stimulation periods each have a preconditioning stimulation duration during which one or more stimuli are delivered. The preconditioning non-stimulation periods each have a preconditioning non-stimulation duration during which no stimulus is delivered.

Cardioprotective stimulation parameters including the postconditioning stimulation sequence duration, the postconditioning stimulation duration, the postconditioning non-stimulation duration, the preconditioning stimulation sequence duration, the preconditioning stimulation duration, and the preconditioning non-stimulation duration are dependent on the type of the one or more stimuli and the location of the one or more stimulation sites in a body. In one embodiment, these cardioprotective stimulation parameters are statistically determined based on clinical studies. In one embodiment, these cardioprotective stimulation parameters are programmable for each individual patient. The cardioprotective stimulation parameters also include stimulation magnitude parameters controlling the intensity of the one or more stimuli. These stimulation magnitude parameters are programmable for each individual patient and are programmed to values that produce the desirable effect while avoiding overstimulation or unintended effects of stimulation.

In a specific embodiment, electrical stimulation pulses are delivered to skeletal muscles in the pectoral area for cardioprotective effects against cardiac ischemia. The electrical stimulation pulses are substantially similar to cardiac pacing pulses. The electrical stimulation pulses are each controlled by a pulse amplitude and pulse duration. The postconditioning stimulation sequence has a postconditioning stimulation sequence duration in a range of approximately 30 seconds to 1 hour, with approximately 10 minutes being a specific example. The postconditioning stimulation duration is in a range of approximately 5 seconds to 1 minute, with approximately 30 seconds being a specific example. The postconditioning non-stimulation duration is in a range of approximately 5 seconds to 1 minute, with approximately 30 seconds being a specific example. The preconditioning stimulation sequences each have a preconditioning stimulation sequence duration in a range of approximately 10 minutes to 72 hours, with approximately 40 minutes being a specific example. The preconditioning stimulation duration is in a range of approximately 1 minute to 1 hour, with approximately 5 minutes being a specific example. The preconditioning non-stimulation duration is in a range of approximately 1 minute to 1 hour, with approximately 5 minutes being a specific example.

Physiological stress sensor 322 senses a stress-indicating signal indicative of a level of the physiological stress at the one or more stimulation sites. The stress-indicating signal serves as a quantitative indication of the cardioprotective effect resulted from the cardioprotective stimulation. In one embodiment, cardioprotective stimulation controller 316 controls the delivery of the one or more stimuli using the stress-indicating signal. In a specific embodiment, cardioprotective stimulation controller 316 adjusts the cardioprotective stimulation parameters using the stress-indicating signal. In one embodiment, physiological stress sensor 322 is connected to implantable medical device 310 using a wired link or a wireless telemetry link. In another embodiment, physiological stress sensor 322 is part of implantable medical device 310 and contained in the implantable housing.

In one embodiment, physiological stress sensor 322 includes a cardiac sensing circuit to sense an electrogram, and the level of the physiological stress is measured by S-T segment elevation in the electrogram. In another embodiment, physiological stress sensor 322 includes a strain gauge that measures the degree of muscular contraction cause by the cardioprotective stimulation. In another embodiment, physiological stress sensor 322 includes a chemical sensor, such as a pH sensor, to sense a degree of chemical reaction to the cardioprotective stimulation.

In another embodiment, physiological stress sensor 322 includes one or more exertion level sensors each sensing an exertion level being an indication or measure of a physiological response to the cardioprotective stimulation. Examples of the exertion level sensor include a chemical sensor that senses pH value, an oximeter or plethysmography sensor that senses a signal oximetry or plethysmography signal indicative of blood oxygen saturation, an impedance sensor that senses a respiratory signal indicative of minute ventilation sensor or respiratory rate, an time interval detector that detects one or more predetermined type cardiac intervals from one or more electrogram signals, and a temperature sensor that senses body temperature, blood temperature, and/or myocardial temperature. In one embodiment, implantable medical device 310 provides rate-adaptive pacing that uses an exertion level sensor for pacing control. This exertion level sensor is also used as physiological stress sensor 322 for cardioprotective stimulation control.

Figure 4:
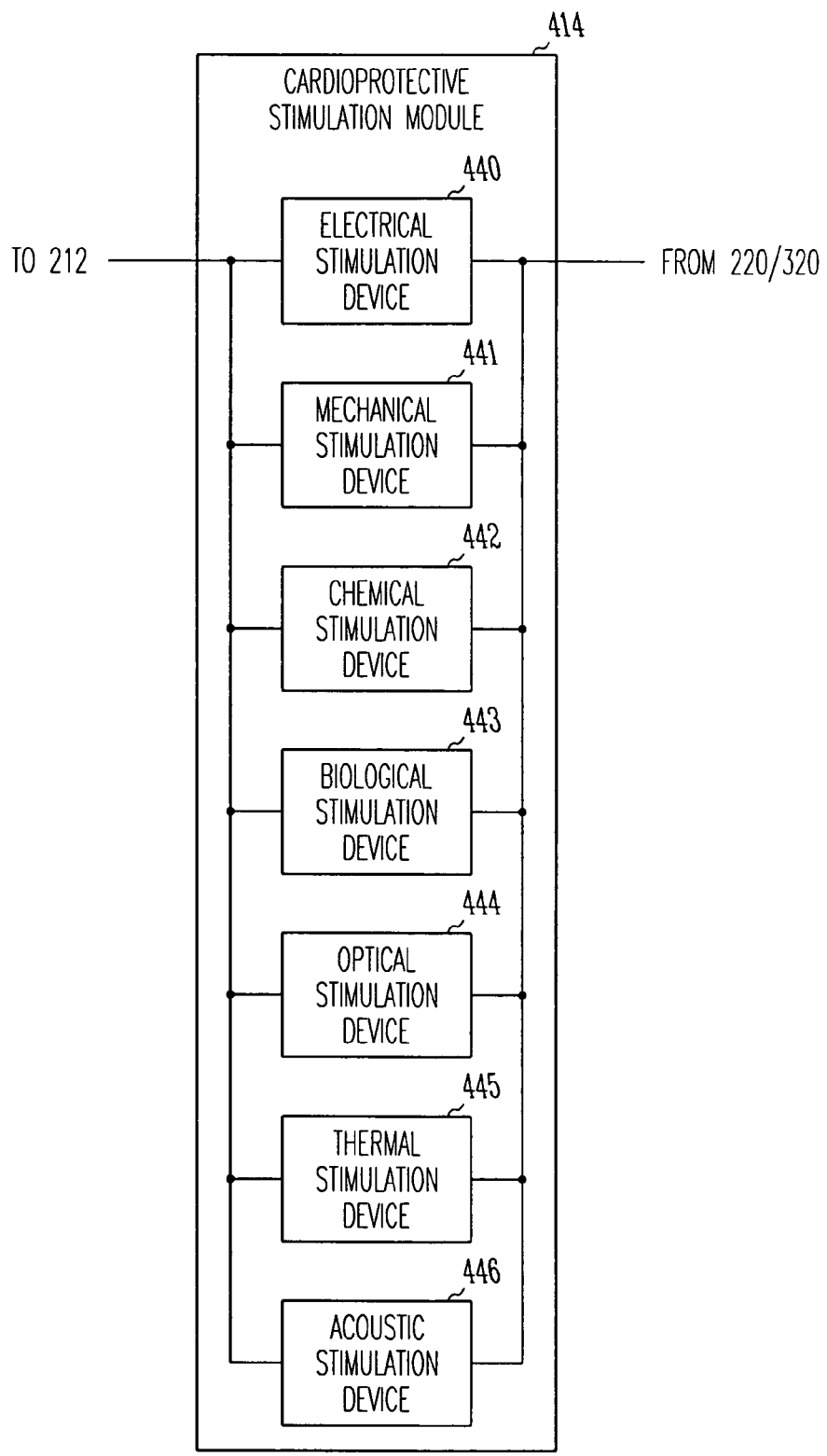
FIG. 4 is a block diagram illustrating an embodiment of a cardioprotective stimulation module of the cardioprotective stimulation system.

FIG. 4 is a block diagram illustrating an embodiment of a cardioprotective stimulation module 414, which represents a specific embodiment of cardioprotective stimulation module 214. In various embodiments, cardioprotective stimulation module 214 includes any one or more illustrated elements of cardioprotective stimulation module 414 as well as other elements that are also capable of eliciting the cardioprotective effects by delivering stimulation to the one or more stimulation sites remote from the ischemic region.

As illustrated in FIG. 4, cardioprotective stimulation module 414 includes an electrical stimulation device 440 that delivers one or more electrical stimuli, a mechanical stimulation device 441 that delivers one or more mechanical stimuli, a chemical stimulation device 442 that delivers one or more chemical stimuli, a biological stimulation device 443 that delivers one or more biologic stimuli, an optical stimulation device 444 that delivers one or more optical stimuli, a thermal stimulation device 445 that delivers one or more thermal stimuli, and an acoustic stimulation device 446 that delivers one or more acoustic stimuli.

Electrical stimulation device 440 includes an electrical stimulation circuit to deliver electrical stimulation pulses. Examples of the electrical stimulation circuit include cardiac pacing circuit, neurostimulation circuit, neuromuscular stimulation circuit, muscular stimulation circuit, and other electrical stimulation circuit capable of activating portions of a body using electrical energy.

Mechanical stimulation device 441 includes a mechanical stress-creating device to create a stress in tissue. Examples of such a mechanical stress-creating device include a device that create a local ischemic condition and a device that creates compression, stretch, or other forms of physical deformation of tissue.

Chemical stimulation device 442 includes a drug delivery device to deliver one or more chemical agents. Examples of such one or more chemical agents include lactic acid to cause early muscle fatigue and other mild acids or bases to alter local pH value.

Biological stimulation device 443 includes a biological agent delivery device to deliver one or more biological agents and/or a gene regulatory device to deliver a gene regulatory signal controlling a gene expression. In one embodiment, the gene regulatory signal controls a regulatable transcriptional element (such as a promoter) of a naturally existing gene. Examples of the gene regulatory device include a light emitter and a heat emitter. In another embodiment, the gene regulatory signal controls a regulatable transcriptional element (such as a promoter) of an artificially introduced gene. The gene regulatory device includes a device that emits any form of energy that regulates the transcriptional element.

Optical stimulation device 444 includes a light emitter to emit a light. In one specific embodiment, the light is a visible light having a wavelength in a range of approximately 390 nanometers to 780 nanometers, with a blue light having a wavelength of approximately 470 nanometers being a specific example. In one embodiment, the light elicits the cardioprotective effect by controlling a gene expression as discussed above with respect to biological stimulation device 443 (i.e., in this embodiment, optical stimulation device 444 represents a specific embodiment of biological stimulation device 443).

Thermal stimulation device 445 includes a thermal emitter to emit a low-intensity electromagnetic wave that rises local tissue temperature at the one or more stimulation sites. In a specific embodiment, the electromagnetic wave has a frequency within the radio frequency (RF) or microwave range. In one embodiment, the rise of temperature elicits the cardioprotective effect by controlling a gene expression as discussed above with respect to biological stimulation device 443 (i.e., in this embodiment, thermal stimulation device 445 represents a specific embodiment of biological stimulation device 443).

Acoustic stimulation device 446 includes an acoustic transducer to transmit an acoustic signal. In one specific embodiment, the acoustic signal is an ultrasonic signal having a wavelength in a range of approximately 1 megahertz to 20 megahertz, with approximately 4 megahertz being a specific example. In one embodiment, the acoustic signal elicits the cardioprotective effect by controlling a gene expression as discussed above with respect to biological stimulation device 443 (i.e., in this embodiment, acoustic signal stimulation device 446 represents a specific embodiment of biological stimulation device 443).

In various embodiments in which system 100 is used to protect non-cardiac tissue or organs against ischemic damage, system 100 includes a structure similar to the cardioprotective stimulation system discussed above, except that ischemia detector 324 detects a non-cardiac ischemic event, and stimulation timer 320 times the delivery of stimulation according to a timing suitable for the specific stimulation site(s). In various embodiments, system 100, 200, or 300 as discussed above are modified for protecting non-cardiac regions from non-cardiac ischemic damage, with ischemia detector 324 adapted to detect a specified type of ischemia and stimulation timer 320 adapted to time a delivery stimulation to one or more specified stimulation sites remote from the region to be protected.

Figure 5:
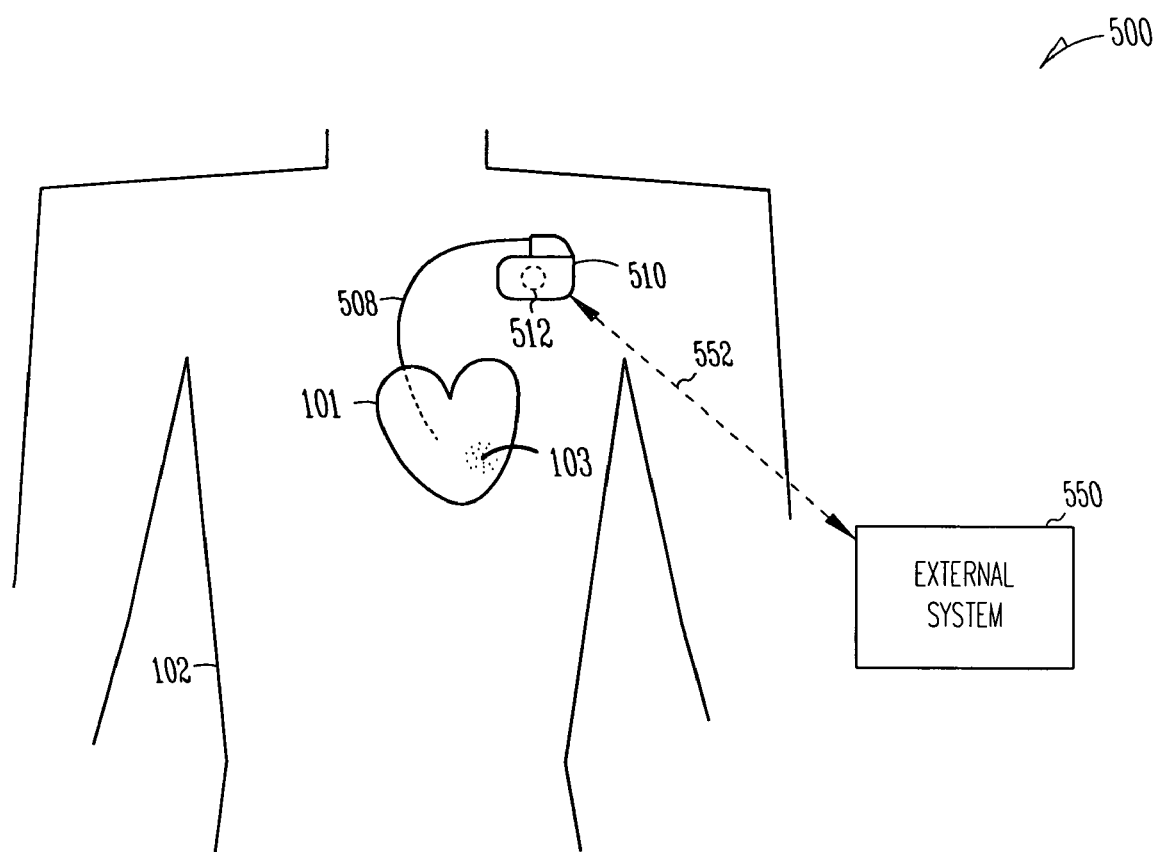
FIG. 5 is an illustration of a cardiac rhythm management (CRM) system including the cardioprotective stimulation system and portions of an environment in which the CRM system is used.

FIG. 5 is an illustration of a CRM system 500 and portions of an environment in which CRM system 500 is used. CRM system 500 includes an implantable medical device 510, an external system 550, and a telemetry link 552 providing for communication between implantable medical device 510 and external system 550. Implantable medical device 510 delivers one or more cardiac electrical therapies to heart 101 through a lead system 508 and a cardioprotective stimulation therapy to one or more stimulation sites in body 102 through a stimulation output device 512 and/or lead system 508. In one embodiment, the one or more stimulation sites are remote from heart 101. In another embodiment, the one or more stimulation sites are within heart 101 but remote from ischemic region 103.

In various embodiments, implantable medical device 510 is an implantable CRM device including one or more of a pacemaker, a cardioverter/defibrillator, a cardiac resynchronization therapy (CRT) device, a cardiac remodeling control therapy (RCT) device, a neurostimulator, a drug delivery device or a drug delivery controller, and a biological therapy device. In various embodiments, lead system 508 includes leads for sensing physiological signals and delivering stimulation pulses, cardioversion/defibrillation shocks, neurostimulation pulses, pharmaceutical agents, biological agents, and/or other types of energy or substance for treating cardiac disorders. In one embodiment, lead system 508 includes one or more stimulation-sensing leads each including at least one electrode placed in or on a heart 101 for sensing electrogram and/or delivering stimulation pulses. In other embodiments, electrodes placed in body 102 but away from heart 101 are used to sense physiological signals and deliver stimulation pulses, cardioversion/defibrillation shocks, neurostimulation pulses, pharmaceutical agents, biological agents, and/or other types of energy or substance for treating cardiac disorders.

Implantable medical device 510 also includes a cardioprotective stimulation system that delivers cardioprotective stimulation through stimulation output device 512. In one embodiment, the cardioprotective stimulation is an electrical stimulation. Stimulation output device 512 includes one or more electrodes incorporated onto the housing of implantable medical device 510. In one embodiment, the one or more electrodes are in contact with the epimysium of pectoral muscle. Implantable medical device 510 delivers cardiac electrical stimulation pulses such as pacing pulses and cardioversion/defibrillation pulses to heart 101 through lead system 508 and cardioprotective electrical stimulation pulses to pectoral muscle through the one or more electrodes on the housing of implantable medical device 510.

External system 550 allows the physician or other caregiver and/or the patient to control the operation of implantable medical device 510 and obtain information acquired by implantable medical device 510. In one embodiment, external system 550 includes a programmer communicating with implantable medical device 510 bi-directionally via telemetry link 552. In another embodiment, external system 550 includes a handheld device communicating with implantable medical device 510 bi-directionally via telemetry link 552. The handheld device allows the patient to start cardioprotective stimulation when the patient feels that an ischemic event has occurred or is going to occur. In another embodiment, external system 550 is a patient management system including an external device communicating with a remote device through a telecommunication network. The external device is within the vicinity of implantable medical device 510 and communicates with implantable medical device 510 bi-directionally via telemetry link 552. The remote device allows the physician or other caregiver to monitor and treat a patient from a distant location. The patient management system is further discussed below, with reference to FIG. 8.

Telemetry link 552 provides for data transmission from implantable medical device 510 to external system 550. This includes, for example, transmitting real-time physiological data acquired by implantable medical device 510, transmitting the ischemia alert signal produced by implantable medical device 510, extracting physiological data acquired by and stored in implantable medical device 510, extracting therapy history data stored in implantable medical device 510, and extracting data indicating an operational status of implantable medical device 510 (e.g., battery status and lead impedance). Telemetry link 552 also provides for data transmission from external system 550 to implantable medical device 510. This includes, for example, programming implantable medical device 510 to acquire physiological data, programming implantable medical device 510 to perform at least one self-diagnostic test (such as for a device operational status), and programming implantable medical device 550 to deliver at least one therapy.

Figure 6:
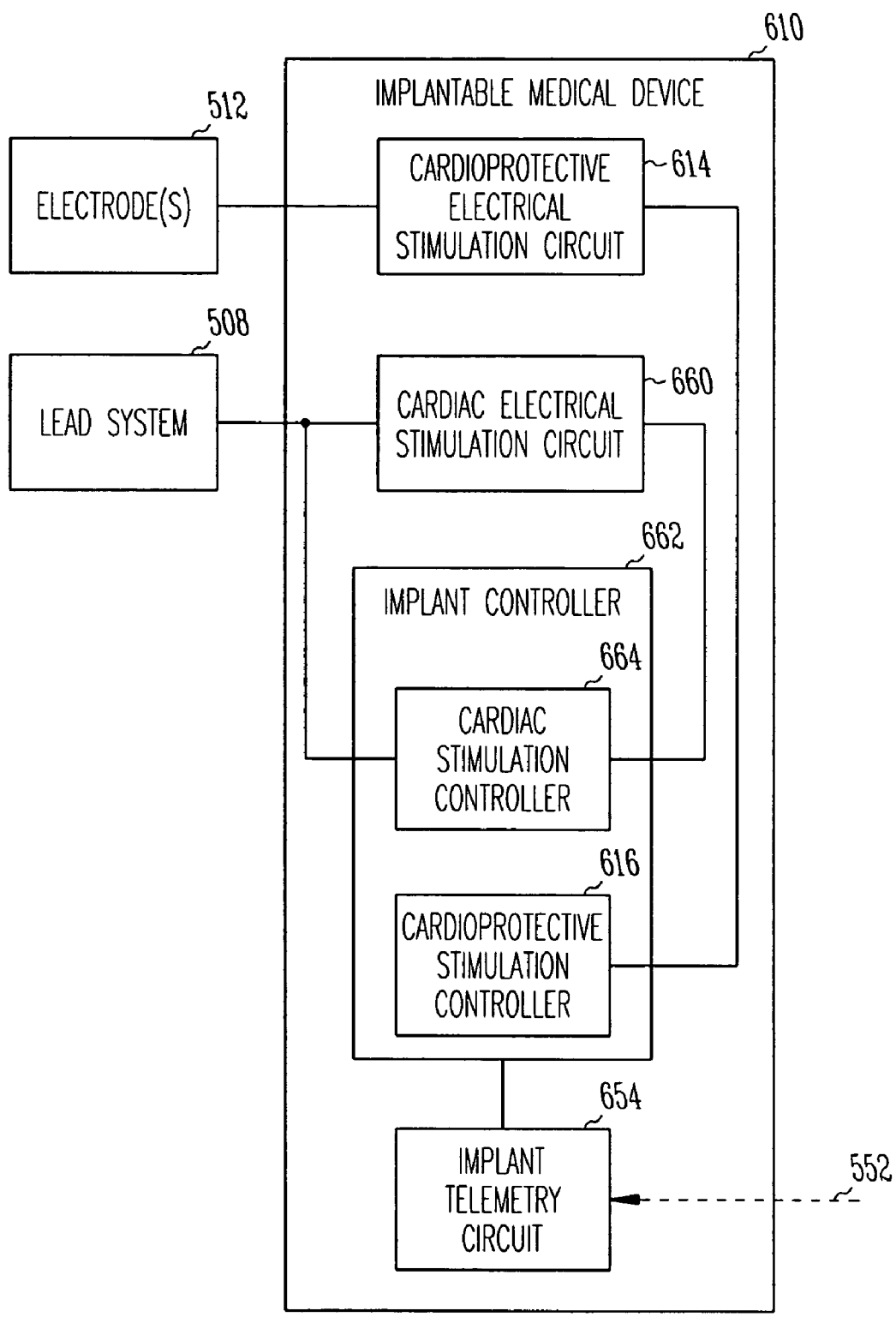
FIG. 6 is a block diagram illustrating an embodiment of portions of circuits of the CRM system.

FIG. 6 is a block diagram illustrating an embodiment of portions of circuits of the implantable elements of CRM system 500. The implantable elements include an implantable medical device 610, electrode(s) 512, and lead system 508. Implantable medical device 610 is a specific embodiment of implantable medical device 510 and includes a cardioprotective electrical stimulation circuit 614, a cardiac electrical stimulation circuit 660, an implant controller 662 that includes a cardiac stimulation controller 664 and a cardioprotective stimulation controller 616, and an implant telemetry circuit 654.

Cardioprotective electrical stimulation circuit 614 is a specific embodiment of cardioprotective stimulation module 214 and delivers electrical stimulation pulses to one or more stimulation sites remote from heart 101 through electrode(s) 512 to elicit a cardioprotective effect against ischemia damages. Cardioprotective stimulation controller 616 controls the delivery of the electrical stimulation pulses from cardioprotective electrical stimulation circuit 614. As a specific embodiment of cardioprotective stimulation controller 216, cardioprotective stimulation controller 616 initiates and times one or more cardioprotective stimulation sequences as discussed above with respect to cardioprotective stimulation controller 216 and 316.

Cardiac electrical stimulation circuit 660 delivers electrical stimulation pulses, such as pacing pulses and cardioversion/defibrillation pulses, to heart 101 through lead system 508. Cardiac stimulation controller 664 controls the delivery of the electrical stimulation pulses from cardiac electrical stimulation circuit 660. In various embodiments, cardiac stimulation controller 664 controls one or more of cardiac electrical therapies including, but not limited to, bradycardia pacing therapy, CRT, RCT, anti-tachycardia pacing therapy, and cardioversion/defibrillation therapy. In various other embodiments, cardiac stimulation controller 664 controls one or more of remote conditioning therapies by delivering electrical stimulation pulses, such as pacing pulses, to heart 101 to protect an ischemic region external to heart 101 from ischemic tissue damage. In one embodiment, a remote conditioning therapy is delivered by pacing heart 101 at a rate that is high enough to create transient cardiac ischemia. Cardiac stimulation controller 664 controls the delivery of pacing pulses to one or more pacing sites in or on heart 101 at a pacing rate programmed to create transient cardiac ischemia. In one embodiment, cardiac stimulation controller 664 controls the delivery of pacing pulses according to a remote conditioning stimulation sequence that includes alternating pacing and non-pacing periods. Each pacing period has a pacing duration during which the pacing pulses are delivered. Each non-pacing period has a non-pacing duration during which no pacing pulse is delivered. Such a remote conditioning stimulation sequence creates an intermittent ischemic condition in heart 101.

Implant telemetry circuit 654 transmits and receives signals through telemetry link 552. In one embodiment, cardioprotective stimulation controller 616 includes an ischemia detector that produces an alert signal when a cardiac ischemic event is detected. Implant telemetry circuit 654 transmits the alert signal to external system 550, which informs the physician or other caregiver and/or the patient that the cardiac ischemic event is detected.

Figure 7:
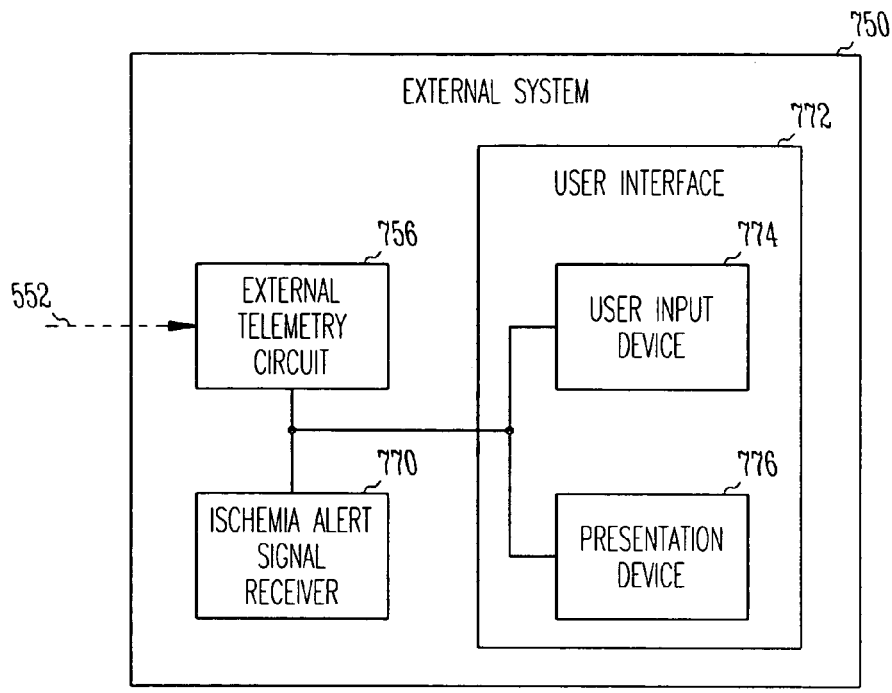
FIG. 7 is a block diagram illustrating an embodiment of portions of a circuit of an external system of the CRM system.

FIG. 7 is a block diagram illustrating an embodiment of portions of a circuit of an external system 750, which is a specific embodiment of external system 550. External system 750 includes an external telemetry circuit 756, an ischemia alert signal receiver 770, and a user interface 772. External telemetry circuit 756 receives and transmits signals through telemetry link 552. Ischemia alert signal receiver 770 receives the alert signal transmitted from implantable medical device 610 when a cardiac ischemic event is detected. User interface 772 includes a user input device 774 and a presentation device 776. User input device 774 allows programming of implantable medical device 510, including the entry of cardioprotective stimulation commands that initiate one or more cardioprotective stimulation sequences and/or parameters of the cardioprotective stimulation. Presentation device 776 includes a display screen. In one embodiment, presentation device 776 further includes a printer and a speaker. In one embodiment, portions of user input device 774 and presentation device 776 are integrated as an interactive screen. Ischemia alert signal receiver 770 receives the ischemia alert signal and, in response, causes presentation device 776 to produce an alarm signal and/or a warning message for the physician or caregiver and/or the patient.

In one embodiment, external system 750 includes a programmer for use by the physician or other caregiver. In another embodiment, external system 750 includes a portable device provided to the patient. In another embodiment, external system 750 is a patient management system that is discussed below with reference to FIG. 8.

Figure 8:
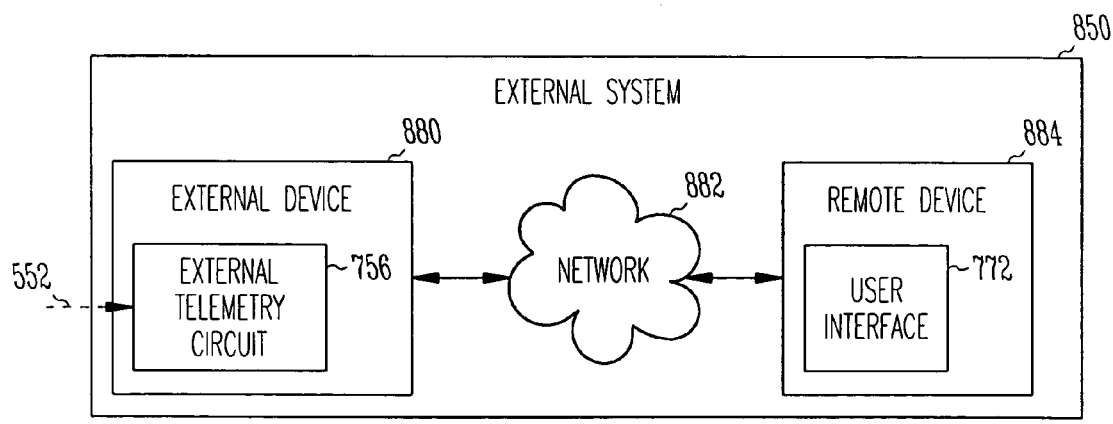
FIG. 8 is a block diagram illustrating an embodiment of the external system.

FIG. 8 is a block diagram illustrating an embodiment of an external system 850, which is a specific embodiment of external system 750. As illustrated in FIG. 8, external system 850 is a patient management system including an external device 880, a telecommunication network 882, and a remote device 884. External device 880 is placed within the vicinity of an implantable medical device and includes external telemetry circuit 756 to communicate with the implantable medical device via telemetry link 552. Remote device 884 is in one or more remote locations and communicates with external device 880 through network 882, thus allowing the physician or other caregiver to monitor and treat the patient from a distant location and/or allowing access to various treatment resources from the one or more remote locations. In one embodiment, as illustrated in FIG. 8, remote device 884 includes user interface 772. This allows the physician or other caregiver to initiate and/or adjust the cardioprotective stimulation in response to the alarm signal and/or warning message associated with the ischemia alert signal.

Figure 9:
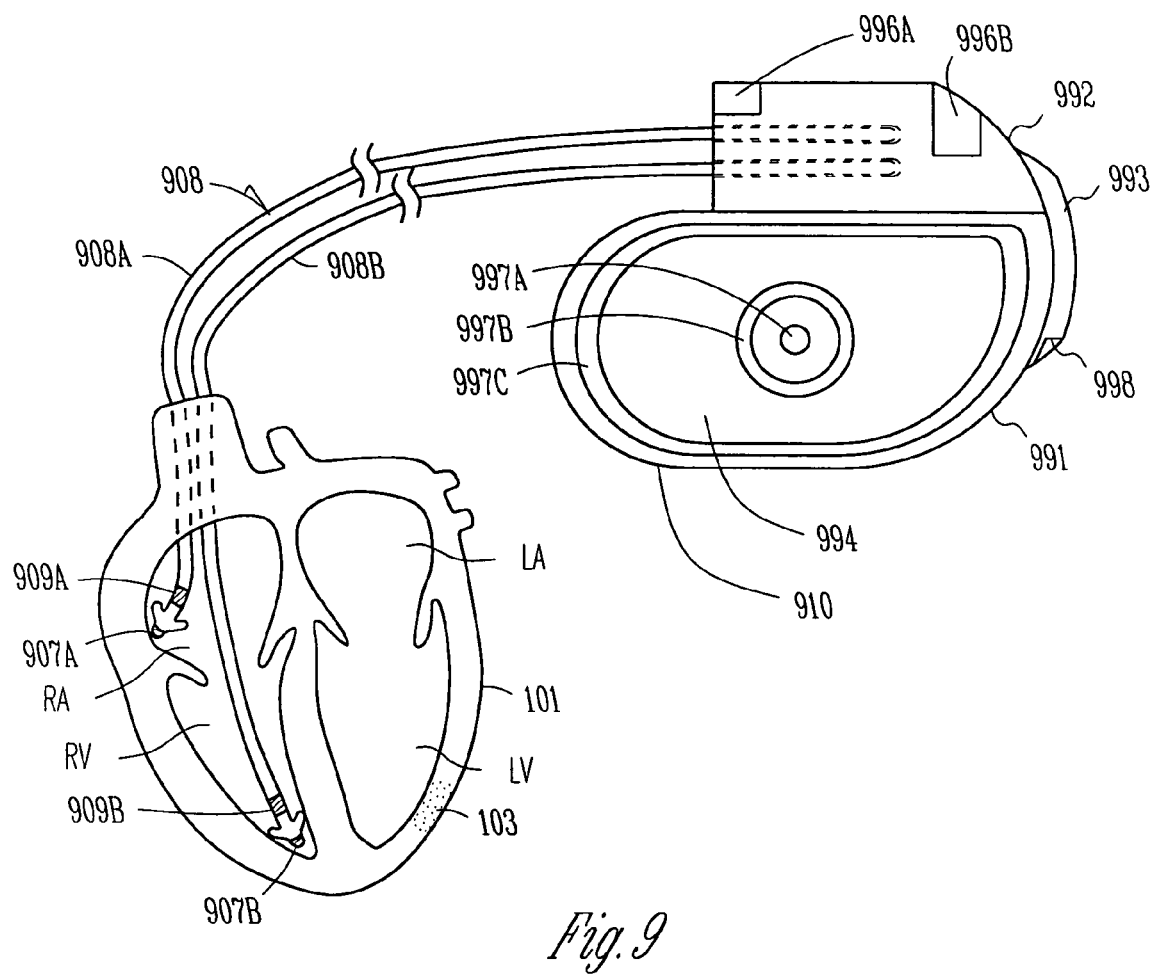
FIG. 9 is a block diagram illustrating an embodiment of stimulation electrodes for cardioprotective stimulation.

FIG. 9 is a block diagram illustrating an embodiment of stimulation electrodes for cardioprotective stimulation. An electrode system for delivering cardioprotective electrical stimulation pulses includes two or more stimulation electrodes. FIG. 9 illustrates examples of stimulation electrodes that allow delivery of cardioprotective electrical stimulation pulses to non-ischemic regions of heart 101 and tissue surrounding implantable medical device 910, which represents a specific embodiment of implantable medical device 110 or 510. In various embodiments, two or more stimulation electrodes are selected from electrodes including, but not limited to, those illustrated in FIG. 9. The selection of the stimulation electrodes is determined by the intended one or more stimulation sites and/or the need to limit the tissue response to a region in close proximity to the one or more stimulation sites.

In one embodiment, one or more pacing electrodes of a lead system 908 are used as one or more stimulation electrodes for the delivery of cardioprotective electrical stimulation pulses. Lead system 908 is a specific embodiment of lead system 508 and, as shown in FIG. 9 for illustrative purposes, includes an atrial lead 908A and a ventricular lead 908B. The one or more stimulation electrodes are selected from, for example, a tip electrode 907A of atrial lead 908A, a ring electrode 909A of atrial lead 908A, a tip electrode 907B of ventricular lead 908B, and a ring electrode 909B of ventricular lead 908B. In one embodiment, the electrode(s) selected for delivering the cardioprotective electrical stimulation pulses are remote from ischemic region 103. Leads 908A-B each have a proximal end connected to implantable medical device 910 and a distal end for intracardiac or epicardial placement. Each tip electrode is located in the distal end of a lead. Each ring electrode is located near the distal end, at a predetermined distance from the tip electrode. In one specific embodiment, atrial lead 908A is an RA lead, and ventricular lead 908B is an RV lead. In another specific embodiment, atrial lead 908A is an RA lead, and ventricular lead 908B is an LV lead. In another specific embodiment, lead system 908 includes only one or more atrial leads. In another specific embodiment, lead system 908 includes only one or more ventricular leads. In other specific embodiments, lead system 908 includes more than one atrial lead and/or more than one ventricular lead.

Implantable medical device 910 includes a hermetically sealed can 991 to house its circuit. Can 991 has an outer surface that is contact with body tissue when implantable medical device 910 is implanted. Can 991 includes or provides for a base of a can electrode 994 that is selectable as one of the stimulation electrodes for the delivery of cardioprotective electrical stimulation pulses. At least a portion of the outer surface of can 991 is made of electrically conductive material. In one embodiment, can 991 is used as can electrode 994. In one specific embodiment, can electrode 994 includes at least one conductive portion of can 991. In another embodiment, can electrode 994 is incorporated onto the outer surface of can 991 and is electrically insulated from any conductive portion of can 991 using a non-conductive layer. In one specific embodiment, a hermetically sealed feedthrough including a conductor provides for an electrical connection between can electrode 994 and the circuit housed in can 991.

A header 992 is attached to can 991 and includes connectors providing for electrical access to the circuit housed in can 991. In one embodiment, one or more header electrodes 996A-B are incorporated into the header. Header electrodes 996A-B are each selectable as one of the electrodes for the delivery of cardioprotective electrical stimulation pulses.

In one embodiment, two or more concentric electrodes 997A-C are incorporated onto the outer surface of can 991. Each of concentric electrodes 997A-C is selectable as one of the stimulation electrodes for the delivery of cardioprotective electrical stimulation pulses. Concentric electrodes 997A-C are insulated from the conductive portion of can 991 with a non-conductive layer and connected to the circuit housed in can 991 via hermetically sealed feedthroughs. In one embodiment, two stimulation electrodes, including an inner electrode and an outer electrode, are selected from concentric electrodes 997A-C for the delivery of cardioprotective electrical stimulation pulses. This limits the tissue response to the stimulation to a region in close proximity to the selected stimulation electrodes. In one embodiment, the outer electrode has a ring shape. In another embodiment, the outer electrode has a shape approaching the contour of can 991. In one embodiment, concentric electrodes 997A-C are incorporated onto the side of can 991 that is in contact with the epimysium of pectoral muscle when implantable medical device 910 is implanted.

In one embodiment, implantable medical device 910 includes an antenna 993 for the far-field RF telemetry. Antenna 993 is electrically connected to the circuit housed in can 991. In one embodiment, antenna 993 projects from header 992 and extends along one side of can 991. In one embodiment, antenna 993 includes a metal conductor with a distal portion exposed for functioning as an antenna electrode 998, which is selectable as one of the stimulation electrodes for the delivery of cardioprotective electrical stimulation pulses.

It is to be understood that the electrodes illustrated in FIG. 9 are intended to be examples but not limitations. Other electrode configurations are usable as long as they allow delivery of the cardioprotective electrical stimulation pulses to the one or more stimulation sites. In one embodiment, the stimulation electrodes for the delivery of cardioprotective electrical stimulation pulses are selected from the electrodes in one or more leads of lead system 908 (e.g., electrodes 907A, 909A, 907B, and 909B). According to the present subject matter, for the purpose of delivering the cardioprotective electrical stimulation pulses, the stimulation electrodes may be remote from ischemic region 103. In another embodiment, the stimulation electrodes for the delivery of cardioprotective electrical stimulation pulses are implantable subcutaneous electrodes. Examples of such implantable subcutaneous electrodes include, but are not limited to electrodes incorporated onto implantable medical device 910, such as can electrode 994, header electrodes 996A-B, concentric electrodes 997A-C, and antenna electrode 998. In a specific embodiment, implantable medical device 910 is for implantation in the pectoral area. Stimulation electrodes are selected for delivering cardioprotective electrical stimulation pulses to cause contraction of the pectoral muscle.

Figure 10:
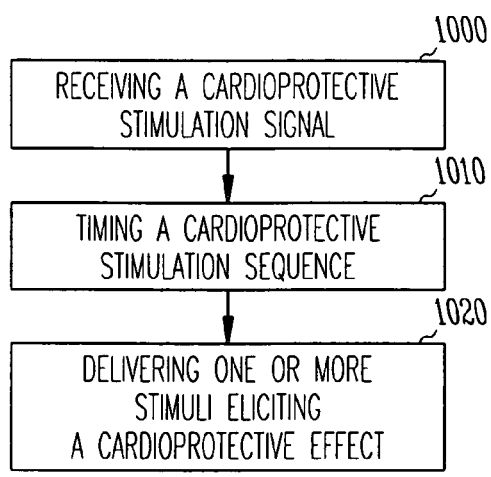
FIG. 10 is a flow chart illustrating an embodiment of a method for cardioprotective stimulation.

FIG. 10 is a flow chart illustrating an embodiment of a method for cardioprotective stimulation. In one embodiment, the method is performed by system 100, including its various embodiments discussed with reference to FIGS. 1-9.

A cardioprotective stimulation signal is received at 1000. The cardioprotective stimulation signal is a triggering signal for initiating a cardioprotective stimulation sequence during which a cardioprotective stimulation therapy is delivered to protect a heart from ischemic damage. In one embodiment, the cardioprotective stimulation signal is issued in response to a detection of a cardiac ischemic event. In another embodiment, the cardioprotective stimulation signal is produced in response to a command issued by a physician or other caregiver or a patient. The command is issued in response to an ischemic event that has occurred, is occurring, or is anticipated to occur.

In response to the received cardioprotective stimulation signal, the cardioprotective stimulation sequence is timed at 1010. The cardioprotective stimulation sequence includes alternating stimulation and non-stimulation periods. Each stimulation period has a stimulation duration during which one or more stimuli are delivered. Each non-stimulation period has a non-stimulation duration during which no stimulus is delivered. The one or more stimuli elicit a cardioprotective effect to protect the heart from tissue damage associated with cardiac ischemic events.

The one or more stimuli are delivered to one or more stimulation sites to elicit the cardioprotective effect at 1020. The one or more stimulation sites include at least one site that is remote from the ischemic region(s) in the heart. In one embodiment, the one or more stimulation sites include at least one site that is remote from the heart.

Figure 11:
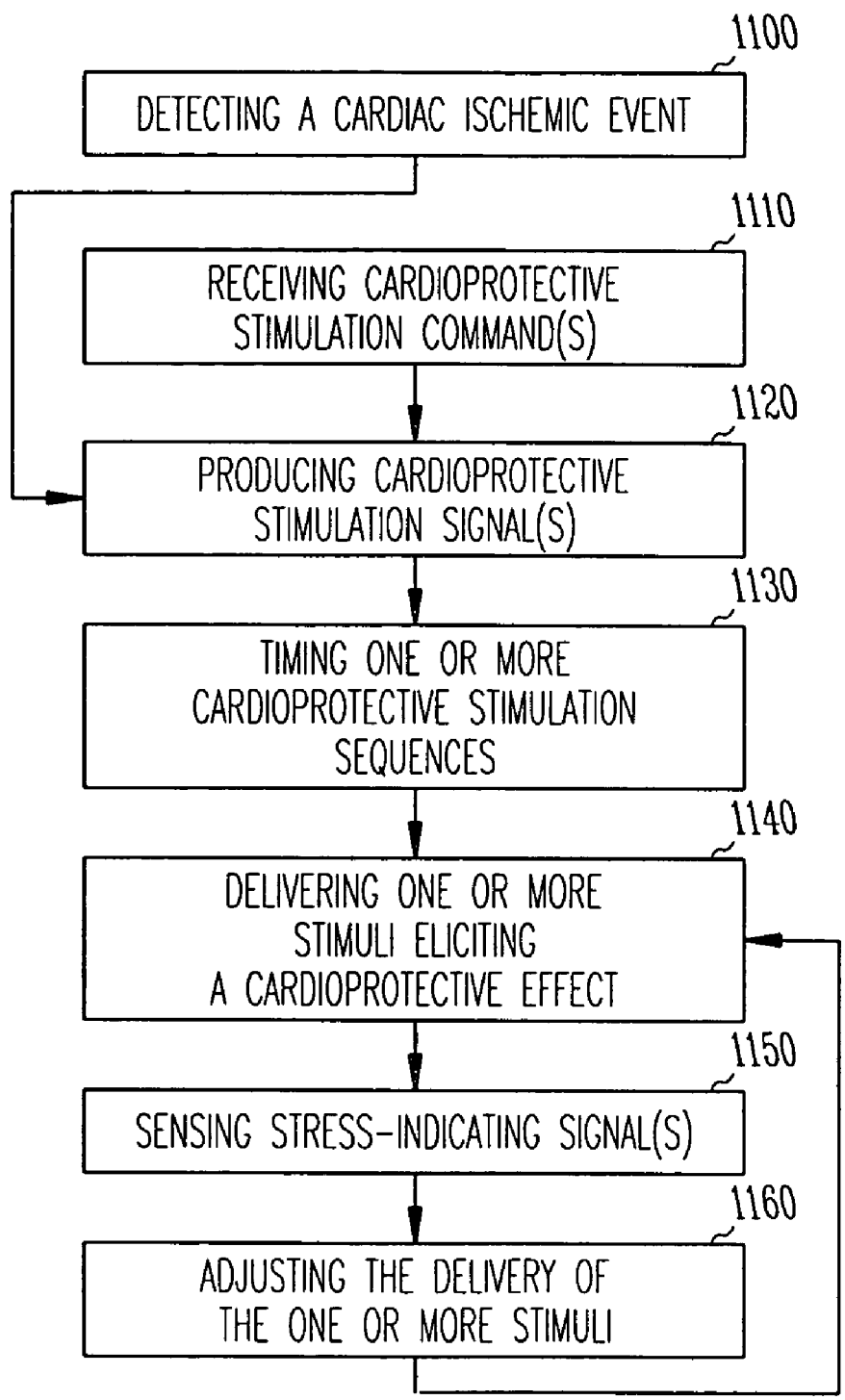
FIG. 11 is a flow chart illustrating a specific embodiment of the method for cardioprotective stimulation.

FIG. 11 is a flow chart illustrating a specific embodiment of the method for cardioprotective stimulation. In one embodiment, the method is performed by system 100, including its various embodiments discussed with reference to FIGS. 1-9.

A cardiac ischemic event is detected at 1100. In one embodiment, one or more physiological signals are sensed, and the cardiac ischemic event is detected from the one or more physiological signals by running an automatic ischemia detection algorithm. In one embodiment, an ischemia alert signal is produced to indicate the detection of the ischemic event to the physician or other caregiver and/or the patient.

A cardioprotective stimulation command is received at 1110. The cardioprotective stimulation command is issued by the physician or other caregiver or the patient. For example, the physician or other caregiver may issue the cardioprotective stimulation command after determining that the patient is at risk of cardiac ischemia, including MI. The patient having a cardiovascular disorder may issue the cardioprotective stimulation command when chest pain is felt. The physician or other caregiver or the patient may also issue the cardioprotective stimulation command upon receiving the ischemia alert signal.

In response to either one or both of the detection of the cardiac ischemic event or the reception of the cardioprotective stimulation command, one or more cardioprotective stimulation signals are produced at 1120. In one embodiment, a postconditioning signal is produced in response to the detection of the cardiac ischemic event. In a specific embodiment, the postconditioning signal is produced when a post-ischemia time interval expires. The post-ischemia time interval starts when the end of the cardiac ischemic event is detected and is up to approximately 10 minutes, with approximately 30 seconds being a specific example. In a specific embodiment, the post-ischemia time interval is chosen such that the postconditioning stimulation sequence is initiated during the reperfusion phase following the cardiac ischemic event. In a further embodiment, a plurality of preconditioning signals is also produced in response to the detection of the cardiac ischemic event. The preconditioning signals are produced after the end of the cardiac ischemic event is detected and the postconditioning stimulation sequence is completed. In a specific embodiment, the preconditioning signals are produced according to a programmed preconditioning schedule, such as on a periodic basis using a predetermined period. The predetermined period is in a range of approximately 24 hours to 72 hours, with approximately 48 hours being a specific example. In another embodiment, the one or more cardioprotective stimulation signals are produced in response to the detection of the cardioprotective stimulation command. In a specific embodiment, a postconditioning signal and a plurality of preconditioning signals are produced in response to the detection of the cardioprotective stimulation command. In another specific embodiment, a postconditioning signal is produced when the detected cardioprotective stimulation command is a postconditioning command, and one or more preconditioning signals are produced when the detected cardioprotective stimulation command is a preconditioning command.

In response to the one or more cardioprotective stimulation signals, one or more cardioprotective stimulation sequences are timed at 1130. In one embodiment, in response to a received postconditioning signal, a postconditioning stimulation sequence is timed. The postconditioning stimulation sequence includes alternating postconditioning stimulation and non-stimulation periods. Each postconditioning stimulation period has a postconditioning stimulation duration during which one or more stimuli are delivered. Each postconditioning non-stimulation periods has a postconditioning non-stimulation duration during which no stimulus is delivered. In one embodiment, in response to each received preconditioning signal, a preconditioning stimulation sequence is timed. Each preconditioning stimulation sequence includes alternating preconditioning stimulation and non-stimulation periods. Each preconditioning stimulation period has a preconditioning stimulation duration during which the one or more stimuli are delivered. Each preconditioning non-stimulation period has a preconditioning non-stimulation duration during which no stimulus is delivered.

The one or more stimuli are delivered during each postconditioning or preconditioning stimulation period to elicit a cardioprotective effect against cardiac ischemia at 1140. The one or more stimuli are delivered to one or more stimulation sites in or on the patient's body. In one embodiment, the one or more stimulation sites are remote from any cardiac ischemic region. In a specific embodiment, the one or more stimulation sites are remote from the patient's heart. In various embodiments, the one or more stimuli create a physiologic stress in the one or more stimulation sites, create a local ischemic condition in the one or more stimulation sites, and/or cause a release of one or more cardioprotective paracrine factors. Examples of the one or more stimuli include one or more electrical stimuli, one or more mechanical stimuli, one or more chemical stimuli, one or more biological stimuli, one or more optical stimuli, one or more thermal stimuli, and one or more acoustic stimuli.

One or more stress-indicating signals are sensed at 1150. Each stress-indicating signal indicates a level of physiologic stress created by the one or more stimuli. Examples of such stress-indicating signals include electrograms indicative of change in cardiac ischemia state caused by the one or more stimuli, a strain gauge signal indicative of muscular response to the one or more stimuli, a chemical sensor signal indicative of a chemical response to the one or more stimuli, and a signal indicative of exertion level. Examples of the signal indicative of exertion level include a signal indicative of blood pH value, a signal indicative of oxygen saturation, a respiratory signal indicative of minute ventilation, a respiratory signal indicative of respiratory rate, a signal indicative time intervals between selected cardiac events, a signal indicative of body temperature, a signal indicative of blood temperature, and a signal indicative of myocardial temperature.

The delivery of the one or more stimuli is adjusted using the sensed one or more stress-indicating signals at 1160. The adjustment ensures that the intended cardioprotective effect is elicited by the one or more stimuli.

The method of cardioprotective stimulation is illustrated in FIGS. 10 and 11 as an example but not a restriction. The present subject matter provides a method for protecting a cardiac or non-cardiac region in a body from ischemic damage by delivering stimulation to one or more stimulation sites remote from the injured region. The injured region is a result from cardiac ischemia or non-cardiac ischemia such as ischemic stroke, ischemic renal failure, ischemia in the central nervous system, and ischemia in the skeletal muscle. The one or mote stimulation sites includes cardiac and non-cardiac sites. That is, the present subject matter provides for a method for protecting a cardiac region from ischemic damage by delivering stimulation to one or more stimulation sites remote from the heart, as well as a method for protecting a non-cardiac region from ischemic damage by delivering stimulation to one or more stimulation sites in or on the heart.

Figure 12:
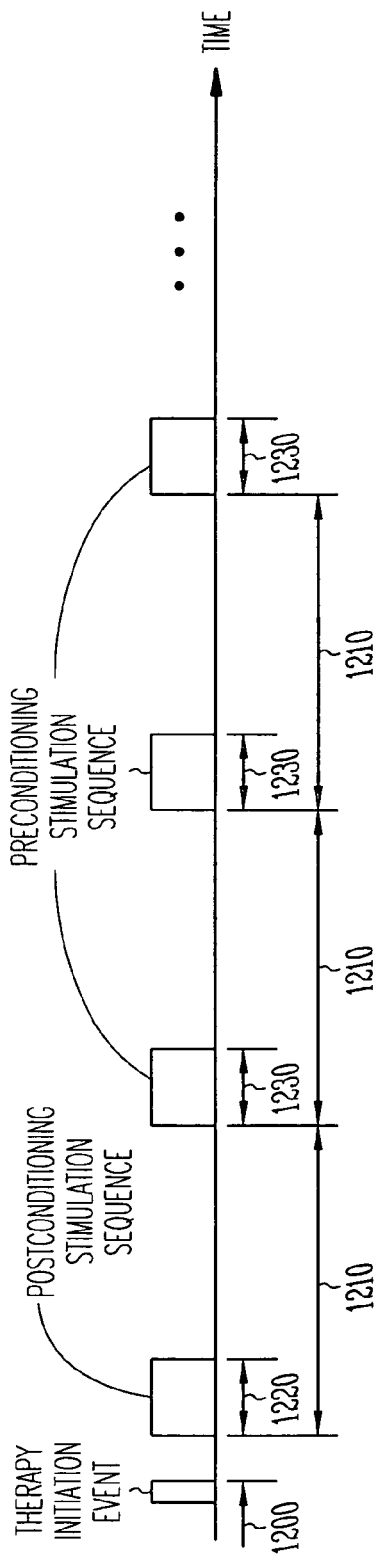
FIG. 12 is an illustration of an embodiment of timing of cardioprotective stimulation sequences.
Figure 13:
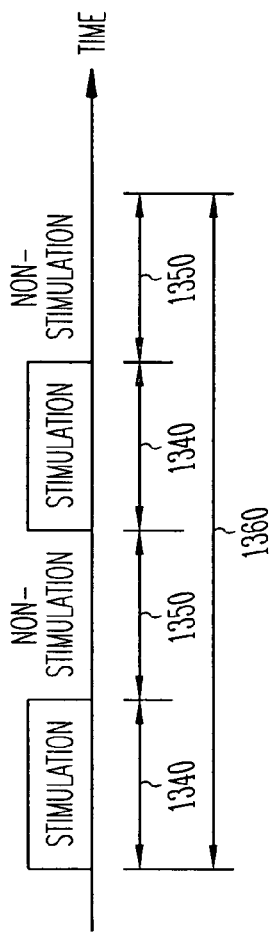
FIG. 13 is an illustration of an embodiment of timing of stimulation and non-stimulation periods during a cardioprotective stimulation sequence.

FIGS. 12 and 13 illustrate various timing intervals discussed above. The timing of the cardioprotective stimulation sequences is illustrated in FIGS. 12 and 13 as an example, but not as a restriction.

FIG. 12 is an illustration of an embodiment of timing of cardioprotective stimulation sequences including a postconditioning stimulation sequence following by preconditioning stimulation sequences. A postconditioning stimulation sequence is initiated in response to a therapy initiation event, such as a detection of a cardiac ischemic event or a reception of a cardioprotective stimulation command. A time interval 1200 starts with the therapy initiation event. When time interval 1200 expires, the postconditioning stimulation sequence is initiated. In one embodiment, the therapy initiation event is the detection of the cardiac ischemic event, and time interval 1200 is a post-ischemia time interval that starts at the end of the ischemic event. The postconditioning stimulation sequence has a postconditioning sequence duration 1220. Then, preconditioning stimulation sequences are initiated on a periodic basis each with a predetermined period 1210. The preconditioning stimulation sequences each have a preconditioning sequence duration 1230.

FIG. 13 is an illustration of an embodiment of timing of stimulation and non-stimulation periods during a cardioprotective stimulation sequence. The cardioprotective stimulation sequence has a sequence duration 1360 and includes alternating stimulation periods 1340 and non-stimulation periods 1350. One or more stimuli are delivered during each of stimulation periods 1340. No stimulus is delivered during each of non-stimulation periods 1350.

Two pairs of alternating stimulation period 1340 and non-stimulation period 1350 are illustrated in FIG. 13 for illustrative but not restrictive purposes. In various embodiments, a cardioprotective stimulation sequence may include one pair of stimulation period 1340 and non-stimulation period 1350, two pairs of stimulation period 1340 and non-stimulation period 1350, or more than two pairs of stimulation period 1340 and non-stimulation period 1350.

In one embodiment, the cardioprotective stimulation sequence is a postconditioning stimulation sequence including alternating postconditioning stimulation and non-stimulation periods. Sequence duration 1360 represents postconditioning sequence duration 1220. Stimulation periods 1340 each represent a postconditioning stimulation period having a postconditioning stimulation duration. Non-stimulation periods 1350 each represent a postconditioning non-stimulation period having a postconditioning non-stimulation duration. In another embodiment, the cardioprotective stimulation sequence is a preconditioning stimulation sequence including alternating preconditioning stimulation and non-stimulation periods. Sequence duration 1360 represents preconditioning sequence duration 1230. Stimulation periods 1340 each represent a preconditioning stimulation period having a preconditioning stimulation duration. Non-stimulation periods 1350 each represent a preconditioning non-stimulation period having a preconditioning non-stimulation duration.

The timing of the cardioprotective stimulation sequences as illustrated in FIGS. 12 and 13 may also be applied as a remote conditioning stimulation sequence for protecting a non-cardiac region by pacing the heart. In one embodiment, a postconditioning pacing sequence is initiated in response to a therapy initiation event, such as a detection of a non-cardiac ischemic event or a reception of a remote conditioning pacing command. A time interval starts with the therapy initiation event. When the time interval expires, a postconditioning pacing sequence is initiated. In one embodiment, the therapy initiation event is the detection of the non-cardiac ischemic event, the time interval is a post-ischemia time interval that starts at the end of the ischemic event. The postconditioning pacing sequence has a postconditioning pacing duration. Then, preconditioning pacing sequences are initiated on a periodic basis each with a predetermined period. The preconditioning pacing sequences each have a preconditioning sequence duration. The postconditioning and preconditioning sequences each have a sequence duration and include alternating pacing and non-pacing periods. Pacing pulses are delivered during each of the pacing periods at a rate that is sufficiently high to induce cardiac ischemia. No pacing pulse is delivered during each of non-pacing periods.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for stimulating at least one stimulation site in a body having a heart, the at least one stimulation site remote from the heart, the system comprising:
    an implantable stimulation output device configured for delivering non-cardiac stimulation to the at least one stimulation site; and
    an implantable medical device including:
        a cardioprotective stimulation module coupled to the implantable stimulation output device, the cardioprotective stimulation module adapted to deliver one or more non-cardiac stimuli to the at least one stimulation site through the implantable output device, the one or more non-cardiac stimuli creating a physiologic stress at the at least one stimulation site without causing myocardial contraction in the heart, the physiologic stress capable of eliciting a cardioprotective effect that protects the heart from tissue damage caused by cardiac ischemia; and a cardioprotective stimulation controller coupled to the cardioprotective stimulation module, the cardioprotective stimulation controller including:
a stimulation initiator including an ischemia detector adapted to detect an end of a cardiac ischemic event, the stimulation initiator adapted to produce cardioprotective stimulation signals in response to a detection of the end of the cardiac ischemic event, the cardioprotective stimulation signals each initiating a cardioprotective stimulation sequence; and
a stimulation timer adapted to time the cardioprotective stimulation sequence in response to each of the cardioprotective stimulation signals, the cardioprotective stimulation sequence including alternating stimulation and non-stimulation periods, the stimulation periods each having a stimulation duration during which the one or more non-cardiac stimuli are delivered, the non-stimulation periods each having a non-stimulation duration during which none of the one or more non-cardiac stimuli is delivered.

2. The system of claim 1, wherein the implantable stimulation output device comprises at least one stimulation electrode, and the cardioprotective stimulation module comprises an electrical stimulation circuit adapted to deliver one or more non-cardiac electrical stimuli through the at least one stimulation electrode.

3. The system of claim 2, wherein the implantable medical device further comprises a cardiac stimulation circuit to deliver cardiac stimulation pulses to the heart.

4. The system of claim 3, wherein the implantable medical device comprises an implantable housing configured to house the cardioprotective stimulation module, the cardioprotective stimulation controller, and the cardiac stimulation circuit, and wherein the at least one electrode is incorporated onto the implantable housing.

5. The system of claim 1, wherein the cardioprotective stimulation module comprises a mechanical stimulation device adapted to deliver one or more mechanical stimuli of the one or more non-cardiac stimuli, the one or more mechanical stimuli creating physical deformation of tissue at the at least one stimulation site.

6. The system of claim 1, further comprising at least one physiological stress sensor adapted to sense a stress-indicating signal indicative of a level of the physiologic stress, and wherein the cardioprotective stimulation controller is adapted to control the delivery of the one or more stimuli creating the physiologic stress using the stress-indicating signal.

7. The system of claim 6, wherein the at least one physiological stress sensor comprises a cardiac sensing circuit adapted to sense an electrogram.

8. The system of claim 6, wherein the at least one physiological stress sensor comprises a chemical sensor adapted to sense a degree of chemical reaction to the non-cardiac stimulation.

9. The system of claim 6, wherein the at least one physiological stress sensor comprises an exertion level sensor to sense an exertion level.

10. The system of claim 9, wherein the exertion level sensor is adapted to sense a pH value.

11. The system of claim 9, wherein the exertion level sensor is adapted to sense an oximetry or plethysmography signal.

12. The system of claim 9, wherein the exertion level sensor is adapted to sense a respiratory signal.

13. The system of claim 9, wherein the exertion level sensor is adapted to sense one or more cardiac time intervals.

14. The system of claim 9, wherein the exertion level sensor is adapted to sense one or more of body temperature, blood temperature, and myocardial temperature.

15. The system of claim 6, wherein the at least one physiological stress sensor comprises a strain gauge adapted to measure a degree of muscular contraction.

16. The system of claim 1, wherein the cardioprotective stimulation module comprises a gene regulatory device to deliver a gene regulatory signal controlling a gene expression.

17. The system of claim 1, wherein the cardioprotective stimulation module comprises one or more of a mechanical stimulation device to deliver one or more mechanical stimuli, a chemical stimulation device to deliver one or more chemical stimuli, a biological stimulation device to deliver one or more biological stimuli, an optical stimulation device to deliver one or more optical stimuli, a thermal stimulation device to deliver one or more thermal stimuli, and an acoustic stimulation device to deliver one or more acoustic stimuli.

18. The system of claim 1, wherein the stimulation initiator is adapted to produce a postconditioning signal in response to a detection of the end of the cardiac ischemic event, the postconditioning signal being one of the cardioprotective stimulation signals.

19. The system of claim 18, wherein the stimulation initiator is further adapted to produce a plurality of preconditioning signals in response to the detection of the end of the cardiac ischemic event, the preconditioning signals each being one of the cardioprotective stimulation signals.

20. The system of claim 19, wherein the stimulation initiator is adapted to produce the plurality of preconditioning signals on a periodic basis using a predetermined period in a range of approximately 24 hours to 72 hours.

21. The system of claim 1, wherein the stimulation initiator comprises a stimulation command detector to detect a cardioprotective stimulation command and is adapted to produce one or more of the cardioprotective stimulation signals in response to the detection of the cardioprotective stimulation command.

22. The system of claim 21, further comprising an external system communicatively coupled to the implantable medical device, the external system adapted to transmit the cardioprotective stimulation command.

23. The system of claim 22, wherein the external system comprises:
a user interface device to receive a user command; and
an external controller to produce the cardioprotective stimulation command in response to the user command.

24. The system of claim 23, wherein the external system comprises a handheld device.

25. The system of claim 1, wherein the cardioprotective stimulation module comprises an electrical stimulation device adapted to deliver one or more electrical stimuli.

26. The system of claim 1, wherein the cardioprotective stimulation module comprises a chemical stimulation device adapted to deliver one or more chemical stimuli.

27. The system of claim 1, wherein the cardioprotective stimulation module comprises a biological stimulation device adapted to deliver one or more biological stimuli.

28. The system of claim 1, wherein the cardioprotective stimulation module comprises an optical stimulation device adapted to deliver one or more optical stimuli.

29. The system of claim 1, wherein the cardioprotective stimulation module comprises a thermal stimulation device adapted to deliver one or more thermal stimuli.

30. The system of claim 1, wherein the cardioprotective stimulation module comprises and an acoustic stimulation device adapted to deliver one or more acoustic stimuli.

31. A system for stimulating at least one stimulation site in a body having a heart, the at least one stimulation site remote from the heart, the system comprising:
- an implantable stimulation output device configured for delivering non-cardiac stimulation to the at least one stimulation site; and
- an implantable medical device including:
  - a cardioprotective stimulation module coupled to the implantable stimulation output device, the cardioprotective stimulation module adapted to deliver one or more non-cardiac stimuli to the at least one stimulation site through the implantable output device, the one or more non-cardiac stimuli creating a physiologic stress at the at least one stimulation site without causing myocardial contraction in the heart, the physiologic stress capable of eliciting a cardioprotective effect against cardiac ischemia; and
  - a cardioprotective stimulation controller coupled to the cardioprotective stimulation module, the cardioprotective stimulation controller including:
    - a stimulation initiator including an ischemia detector adapted to detect an end of a cardiac ischemic event, the stimulation initiator adapted to produce cardioprotective stimulation signals after the end of the cardiac ischemic event is detected, the cardioprotective stimulation signals each initiating a cardioprotective stimulation sequence; and
    - a stimulation timer adapted to time the cardioprotective stimulation sequence in response to each of the cardioprotective stimulation signals, the cardioprotective stimulation sequence including alternating stimulation and non-stimulation periods, the stimulation periods each having a stimulation duration during which the one or more non-cardiac stimuli are delivered, the non-stimulation periods each having a non-stimulation duration during which none of the one or more non-cardiac stimuli is delivered,
    - wherein the stimulation initiator is adapted to produce a postconditioning signal when a post-ischemia time interval expires, the post-ischemia time interval starting when the end of the cardiac ischemic event is detected, the postconditioning signal being one of the cardioprotective stimulation signals.

32. A system for stimulating at least one stimulation site in a body having a heart, the at least one stimulation site remote from the heart, the system comprising:
- an implantable stimulation output device configured for delivering non-cardiac stimulation to the at least one stimulation site; and
- an implantable medical device including:
  - a cardioprotective stimulation module coupled to the implantable stimulation output device, the cardioprotective stimulation module adapted to deliver one or more non-cardiac stimuli to the at least one stimulation site through the implantable output device, the one or more non-cardiac stimuli creating a physiologic stress at the at least one stimulation site without causing myocardial contraction in the heart, the physiologic stress capable of eliciting a cardioprotective effect against cardiac ischemia; and
  - a cardioprotective stimulation controller coupled to the cardioprotective stimulation module, the cardioprotective stimulation controller including:
    - a stimulation initiator including an ischemia detector adapted to detect an end of a cardiac ischemic event, the stimulation initiator adapted to produce cardioprotective stimulation signals after the end of the cardiac ischemic event is detected, the cardioprotective stimulation signals each initiating a cardioprotective stimulation sequence; and
    - a stimulation timer adapted to time the cardioprotective stimulation sequence in response to each of the cardioprotective stimulation signals, the cardioprotective stimulation sequence including alternating stimulation and non-stimulation periods, the stimulation periods each having a stimulation duration during which the one or more non-cardiac stimuli are delivered, the non-stimulation periods each having a non-stimulation duration during which none of the one or more non-cardiac stimuli is delivered,
    - wherein the stimulation initiator is adapted to produce a postconditioning signal within approximately 10 minutes after the end of the cardiac ischemic event is detected, the postconditioning signal being one of the cardioprotective stimulation signals.

* * * * *